US009233175B2

(12) United States Patent
Low et al.

(10) Patent No.: US 9,233,175 B2
(45) Date of Patent: *Jan. 12, 2016

(54) METHODS OF IMAGING INFLAMMATORY DISEASES BY LIGANDS CONJUGATED TO FLUORESCENT COMPOUNDS

(71) Applicant: Purdue Research Foundation, West Lafayette, IN (US)

(72) Inventors: Philip S. Low, West Lafayette, IN (US); Sumith A. Kularatne, West Lafayette, IN (US); Lindsay E. Kelderhouse, Island Lake, IL (US); Sakkarapalayam M. Mahalingam, West Lafayette, IN (US)

(73) Assignee: Purdue Research Foundation, West Lafayette, IN (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/135,099

(22) Filed: Dec. 19, 2013

(65) Prior Publication Data

US 2014/0271484 A1 Sep. 18, 2014

Related U.S. Application Data

(60) Provisional application No. 61/791,921, filed on Mar. 15, 2013.

(51) Int. Cl.
*A61K 49/00* (2006.01)
*G01N 33/569* (2006.01)
*G01N 33/566* (2006.01)
*G01N 33/50* (2006.01)

(52) U.S. Cl.
CPC .......... *A61K 49/0052* (2013.01); *A61K 49/0032* (2013.01); *A61K 49/0034* (2013.01); *G01N 33/5091* (2013.01); *G01N 33/566* (2013.01); *G01N 33/56966* (2013.01)

(58) Field of Classification Search
CPC .......... A61K 49/0032; A61K 49/0034; A61K 49/0052
USPC .......... 424/9.1, 9.2, 9.341, 9.6; 544/257, 258, 544/260, 279, 287
See application file for complete search history.

(56) References Cited

U.S. PATENT DOCUMENTS

| 4,337,339 | A | * | 6/1982 | Farina et al. ................. 544/257 |
| 7,547,721 | B1 | | 6/2009 | Miwa et al. |
| 8,044,200 | B2 | | 10/2011 | Xu |
| 2011/0165075 | A1 | | 7/2011 | Rajopadhye |
| 2012/0003151 | A1 | | 1/2012 | Low et al. |
| 2012/0164635 | A1 | | 6/2012 | Pham |
| 2013/0039860 | A1 | * | 2/2013 | Cheung .......................... 424/9.6 |

FOREIGN PATENT DOCUMENTS

| WO | WO2007/139815 | A2 | | 12/2007 |
| WO | WO-2007139815 | | * | 12/2007 |
| WO | 2013/130776 | A1 | | 9/2013 |

OTHER PUBLICATIONS

PCT, Notification of Transmittal of the International Search Report and the Written Opinion of the International Searching Authority, or the Declaration, in International application No. PCT/US13/76659 dated Apr. 4, 2014. (21 pages).
International Search Report in PCT/US13/56629 dated May 13, 2014.

* cited by examiner

*Primary Examiner* — Michael G Hartley
*Assistant Examiner* — Jagadishwar Samala
(74) *Attorney, Agent, or Firm* — McAndrews, Held & Malloy, Ltd.

(57) ABSTRACT

The present disclosure relates to compounds that are useful as near-infrared fluorescence probes, wherein the compounds include i) a pteroyl ligand that binds to a target receptor protein, ii) a dye molecule, and iii) a linker molecule that comprises an amino acid or derivative thereof. The disclosure further describes methods of imaging of inflammatory diseases using the compounds.

27 Claims, 8 Drawing Sheets

METHODS OF IMAGING INFLAMMATORY DISEASES BY LIGANDS CONJUGATED TO FLUORESCENT COMPOUNDS

RELATED APPLICATIONS

The present patent application claims the priority benefit of U.S. Provisional Patent Application No. 61/791,921, filed Mar. 15, 2013; U.S. patent application Ser. No. 14/010,098 filed Aug. 26, 2013; PCT International Patent Application No. PCT/US13/56,629, filed Aug. 26, 2013, and U.S. patent application Ser. No. 14/046,916, filed Oct. 4, 2013. The content of each of the aforementioned applications is hereby incorporated by reference in its entirety into this disclosure.

TECHNICAL FIELD

The present disclosure relates to methods of treating inflammatory diseases, and compositions and compounds for use therein. This disclosure provides methods of utilizing pterin derivative ligands conjugated to dyes for the targeted imaging of inflammatory diseases. Conjugation of pterin derivative ligands to dyes using amino acid linking groups increase specificity and detection of the compound. Methods of treatment of inflammatory diseases using the conjugated compounds involving use thereof in diagnostic imaging are contemplated.

BACKGROUND

Chronic inflammatory diseases affect millions of people daily. Patients undergo treatment of inflammatory diseases with varied results and many have a recurrence of locoregional or systemic disease throughout their lifetime. Despite major advances in the immunology field over the last decade, there are hurdles to overcome in the field, including, for example, improved patient quality of life by effective and preferably non-surgical ways of target-specific identification of the disease(s).

While the immune system normally provides a line of defense against foreign pathogens, there are many instances where the immune response itself is involved in the progression of disease. Diseases caused or worsened by a person's own immune response are autoimmune diseases such as multiple sclerosis, lupus erythematosus, psoriasis, pulmonary fibrosis, and rheumatoid arthritis and diseases in which the immune response contributes to pathogenesis such as atherosclerosis, inflammatory diseases, osteomyelitis, ulcerative colitis, Crohn's disease, and graft versus host disease (GVHD) often resulting in organ transplant rejection. Additional exemplary disease states include fibromyalgia, osteoarthritis, sarcoidosis, systemic sclerosis, Sjogren's syndrome, inflammations of the skin (e.g., psoriasis), glomerulonephritis, proliferative retinopathy, restenosis, and chronic inflammations.

Activated inflammatory cells, such as macrophages, can contribute to the pathophysiology of disease in some instances. Activated inflammatory cells can nonspecifically engulf and kill foreign pathogens within the cells by hydrolytic and oxidative attack resulting in degradation of the pathogen. Peptides from degraded proteins can be displayed on the inflammatory cell surface where they can be recognized by T cells, and they can directly interact with antibodies on the B cell surface, resulting in T and B cell activation and further stimulation of the immune response. Inflammatory cell types that may be associated with inflammatory disease states include macrophages, monocytes, and progenitor cells, including endothelial progenitor cells.

The folate receptor (FR) is a 38 KDa GPI-anchored protein that binds the vitamin folic acid with high affinity (<1 nM). Following receptor binding, rapid endocytosis delivers the vitamin into the cell, where it is unloaded in an endosomal compartment at low pH. Importantly, covalent conjugation of small molecules, proteins, and even liposomes to folic acid does not alter the vitamin's ability to bind the folate receptor, and therefore, folate-drug conjugates can readily enter cells by receptor-mediated endocytosis.

Because most cells use an unrelated reduced folate carrier (RFC) to acquire the necessary folic acid, expression of the folate receptor is restricted to a few cell types. With the exception of kidney and placenta, normal tissues express low or nondetectable levels of FR. Folate binds to its cognate receptor (major isoforms: FR-α, FR-β, FR-γ and FR-δ) with high affinity (Kd<0.5 nM) and specificity. FR-α, overexpressed in 80% of all malignant cell types (e.g., ovarian, lung, breast, kidney) and FR-β, expressed in unique subsets of activated macrophages and certain hematological malignancies, constitute the two primary FR isoforms exploited for delivery of targeted therapeutic and imaging payloads. It has also been reported that FR-β, the nonepithelial isoform of the folate receptor, is expressed on activated (but not resting) synovial macrophages.

A folate-targeted single-photon emission computed tomography (SPECT) imaging agent (EC20) has been recently evaluated by Mary Jo Turk et al. (Arthritis & Rheumatism, Vol. 46, No. 7, July 2002, pp 1947-1955) to determine whether overexpression of a high-affinity folate receptor beta (FR-β) on activated macrophages can be exploited to selectively target imaging agents to sites of inflammation in rats with adjuvant-induced arthritis (AIA). Preclinical studies with such radio imaging agents emphasized the value of imaging arthritic tissues in vivo. The results suggest that it may also be useful for assaying the participation of activated macrophages in inflammatory processes such as rheumatoid arthritis. The same radio imaging agent (EC20) was more recently used to image atherosclerosis by audioradiography in apoliprotein E knockout mice by Wilfredo Ayalo Lopez et al. (The Journal of Nuclear Medicine, Vol. 51, No. 5, May 2010, pp 768-774) for the early detection of heart disease. However, some of the current radio imaging agents are not readily available and expensive, are difficult to model may lack the sensitivity for receptor-based imaging or may have undesirable half-lives or relatively short relaxation times.

Additional studies (Chrystal M Paulos et al., Arthritis Research & Therapy, 2006, 8:R77) have shown that folate-linked radiopharmaceuticals concentrate in arthritic joints, enabling visualization of such tissues by gamma scintigraphy. Selective removal of activated macrophages with folate-linked drugs could be exploited to treat Rheumatoid Arthritis with little toxicity to other tissues.

Immunotherapy treatment studies of another inflammatory disease, systemic lupus erythematosis (SLE), have also previously been performed where activated macrophages have been targeted with known folate-linked hapten conjugates (Bindu Varghese et al., Molecular Pharmaceutics, 4(5):679-85 2007).

EC-20 has also been used to detect FR+ macrophages accumulated at sites of infectious disease by gamma scintigraphic imaging of bacterial infection foci after infecting BALB/c mice with *Staphylococcus aureus*

EC20 also has been used in the clinic to evaluate the RA joints in RA patients (Assessment of disease activity in rheumatoid arthritis using a novel folate targeted radiopharmaceutical Folatescan. Matteson E L, Lowe V J, Prendergast F G, Crowson C S, Moder K G, Morgenstern D E, Messmann R A, Low P S. Clin Exp Rheumatol. 2009 March-April; 27(2): 253-9.)

Although SPECT scans are inexpensive, SPECT scans provide low resolution images when compared with PET scans. Therefore, multiple folate-targeted PET imaging agents are being evaluated in the preclinical stage, including several fluorine-18-labeled agents. However, the radionuclides used in PET imaging could possess either potential dosimetry issues due to their long half-lives [e.g. 86Y ($t_{1/2}$~14.7 h), $^{64}$Cu ($t_{1/2}$~12.7 h), and $^{66}$Ga ($t_{1/2}$~9.49 h)] or their requirement for on-site production due to their short half-lives [e.g. $^{11}$C ($t_{1/2}$~22 minutes), $^{13}$N ($t_{1/2}$~10 min), and $^{15}$O ($t_{1/2}$~2 min)]. Thus, major deficiencies exist in radioimaging.

Since radio imaging agents can damage the DNA that can lead to cancer, use of multiple doses of radio imaging agents are undesirable when monitoring response to therapy. Another disadvantage of radio imaging agents is that the patient has to stay in the hospital until the radio imaging agent clears through the body. Moreover, radioimaging agents can be expensive, may require on-site production, may not be able to store due to half-lives of the radionuclides. Therefore, there is a high medical demand to develop better and safer modalities for detection. In this regard, optical imaging offers many advantages over radio imaging, for instance, ease of synthesis, high purity, long term stability during storage, stability during the preparation, and a reasonable procedure for its synthesis and purification. Moreover, optical imaging agents are safe in clinical use.

Conventional fluorescent techniques use probes in the visible light spectrum (~400-600 nm). Such a wavelength is not optimal to image inflammatory diseases as it is associated with a relatively high level of nonspecific background interference due to collagen in the tissues. Hence the signal to noise ratio from these conventional compounds is low. Moreover, the absorption of visible light by biological chromophores, in particular hemoglobin, limits the penetration depth of the fluorescent image penetration to a few millimeters. Thus disease sites that are buried deeper than a few millimeters in the tissue often remain undetected.

The combination of light absorption by hemoglobin in the visible light spectrum (<600 nm) and water and lipids in the IR range (>900 nm), offers an optical imaging window from approximately 650-900 nm in which the absorption coefficient of tissue is at a minimum. A suitable alternative to dyes that emit light in the visible range would be to develop dyes that can be used in the near infra red (NIR) range because light in the near infrared region induces very little autofluorescence and permeates tissue much more efficiently. Another benefit to near-IR fluorescent technology is that the background from the scattered light from the excitation source is greatly reduced since the scattering intensity is proportional to the inverse fourth power of the wavelength. Low background fluorescence is necessary for highly sensitive detection. Furthermore, the optically transparent window in the near-IR region (650 nm to 900 nm) in biological tissue makes NIR fluorescence a valuable technology for in vivo imaging and subcellular detection applications that require the transmission of light through biological components.

While the use of light in the NIR range for deeper tissue imaging is preferable to light in the visible spectrum, the NIR imaging dyes currently used in the art suffer from a number of challenges and disadvantages. These include a susceptibility to photobleaching, poor chemical stability, absorbance and emission spectra that fall within the same range as many physiological molecules (resulting in high background signal and autofluorescence). Moreover, most of the NIR dyes are not stable during the synthesis, not least due to the fact that conjugating to a ligand with an amine linker leads to multiple unwanted side products. Therefore, taking ligand-targeted NIR imaging agent for clinic can be expensive. Thus, current imaging methods that utilize NIR fluorescent probes for treatment of inflammatory diseases suffer from several drawbacks including being ineffective for deep tissue imaging (>5 mm from the surface); ineffective in quantifying fluorescence signal in mammalian tissues, and in production cost that increase preclinical-to-clinical translational time.

Progress has been made in using optical imaging agents that fluoresce in the near infrared spectral range. Previous advances have also included using non-targeted dyes as optimal contrast agents in the NIR-fluorescence spectral range of about 650 to about 1000 nm to identify inflammatory diseases, including rheumatoid arthritis. This included using cyanine dyes of the class of indotricarbocyanines, such as indocyanine green (ICG) known for its effectiveness in cardiovascular diagnostics and hepatic functional tests. While non-targeted fluorescent dyes have been shown to passively accumulate in some tissues, the resulting tissue-to-background ratios are often poor and the boundaries between inflammatory site and healthy tissues can be difficult to define.

Current research in NIR-fluorescence has led to new approaches for targeted imaging of inflammatory disease. Protease-activated NIRF probes have been studied in vivo for their ability to image the presence of collagen-induced arthritis in joints by targeting a particular cleavage site and resulting in fluorescence activation (Andreas Wunder et al., Arthritis & Rheumatism, 50(8):2459-2465 (2004)). Additionally, a recently developed NIR2-folate conjugate was tested for in vivo imaging of arthritis by targeting an abundance of folate receptors on activated macrophages in inflamed cells (Wei-Tsung Chen et al., Arthritis Research & Therapy, 7(2):R310-R317 (2005)).

However, NIR fluorescent dye-linker-ligand conjugate that comprise alternative folic acid derivatives as ligands with linkers to make better and brighter dyes have not been investigated for targeting inflammatory diseased tissue.

Thus, there remains a need for the use of alternative folic acid derivative-based-dye substances that can be used to specifically target inflammatory-diseased states and that have increased stability and brightness for use in vivo for imaging.

BRIEF SUMMARY OF THE DISCLOSURE

This disclosure provides methods for treating inflammatory diseases by using effective amounts of amino acid linking groups that are conjugated to a compound used for the targeted imaging of inflamed tissue and lymph nodes.

In one embodiment of the invention, this disclosure relates to a method of imaging an inflammatory disease comprising the steps of: a) administering to a patient in need of such a process an effective amount of a compound capable of binding to an inflammatory cell having the formula:

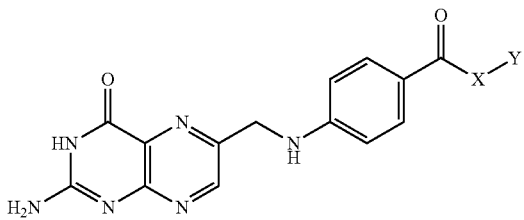

or a pharmaceutically acceptable salt or isotope thereof, wherein X is an amino acid or a derivative thereof, and Y is a dye that has a fluorescence excitation and emission spectra in the near infra red (NIR) range, and the compound maintains or enhances the fluorescence of the dye; and b) fluorescent imaging of an area of the inflammatory disease in the patient's body where the compound has been absorbed. The amino acid of the compound may be selected from the group consisting of tyrosine, cysteine, lysine, a derivative of tyrosine, a derivative of cysteine and a derivative of lysine. In a particular embodiment, the amino acid compound is tyrosine, and in a more particular embodiment, the amino acid compound is a derivative of tyrosine selected from the group consisting of:

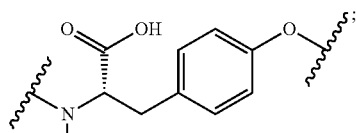

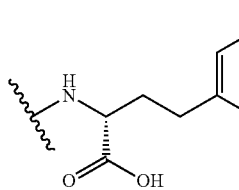

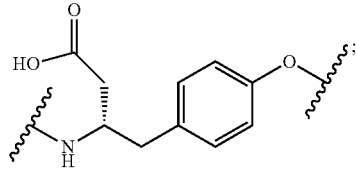

and racemic mixtures thereof.

Additionally, the dye Y of the compound may have the formula:

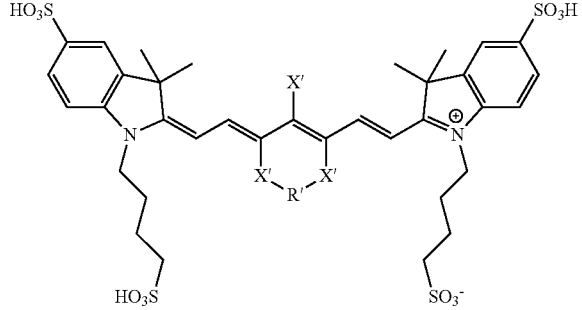

wherein X' is independently selected from the group consisting of O, S, N and C, and R' is independently selected from the group consisting of CH2 and CH2CH2. In particular embodiments, the dye Y is selected from the group consisting of LS288, IR800, SP054, S0121, KODAK, IRD28, S2076, S0456 and derivatives thereof. In a more particular embodiment, the dye Y is S0456.

The inflammatory disease to be imaged may be selected from the group comprising ulcerative colitis, rheumatoid arthritis, pulmonary fibrosis, and atherosclerosis.

The administration of the compound may be by any route conventionally employed. For example it may be by, intravenous (I.V.) injection, intraperitoneal (I.P.) injection, oral administration, etc. into a body part affected by an inflammatory disease. It is envisioned that the route of administration can be topical, enteral, or parenteral. In a second embodiment of the invention, this disclosure provides a method of imaging an inflammatory disease comprising administering to a patient in need of such a process an effective amount of a compound having the formula:

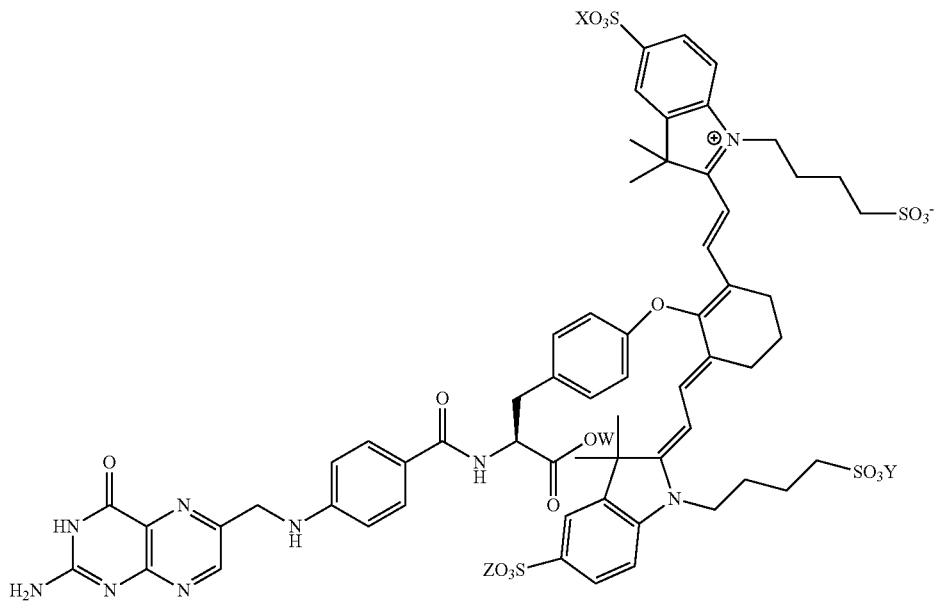

wherein W, X, Y, Z each are H, Na, K⁺ or $NH_4^+$, and fluorescent imaging of an area of the inflammatory disease in the patient's body where the compound has been bound to an inflammatory cell.

Further to this second embodiment, the inflammatory disease to be imaged by this method may be, for example, ulcerative colitis, rheumatoid arthritis, pulmonary fibrosis, and atherosclerosis.

In exemplary embodiments, the administration of the compound may be by intravenous (I.V.) injection, intraperitoneal (I.P.) injection, oral administration, into a body part affected by an inflammatory disease. In particular embodiments, the effective amount of the compound may be between about 1 ng/kg to about 1 mg/kg, and in more particular embodiments 1 μg/kg to about 500 μg/kg, and in a particular embodiment the effective amount of the compound is between about 100 μg/kg to about 400 μg/kg.

DETAILED DESCRIPTION OF THE DISCLOSURE

Figure 1A:
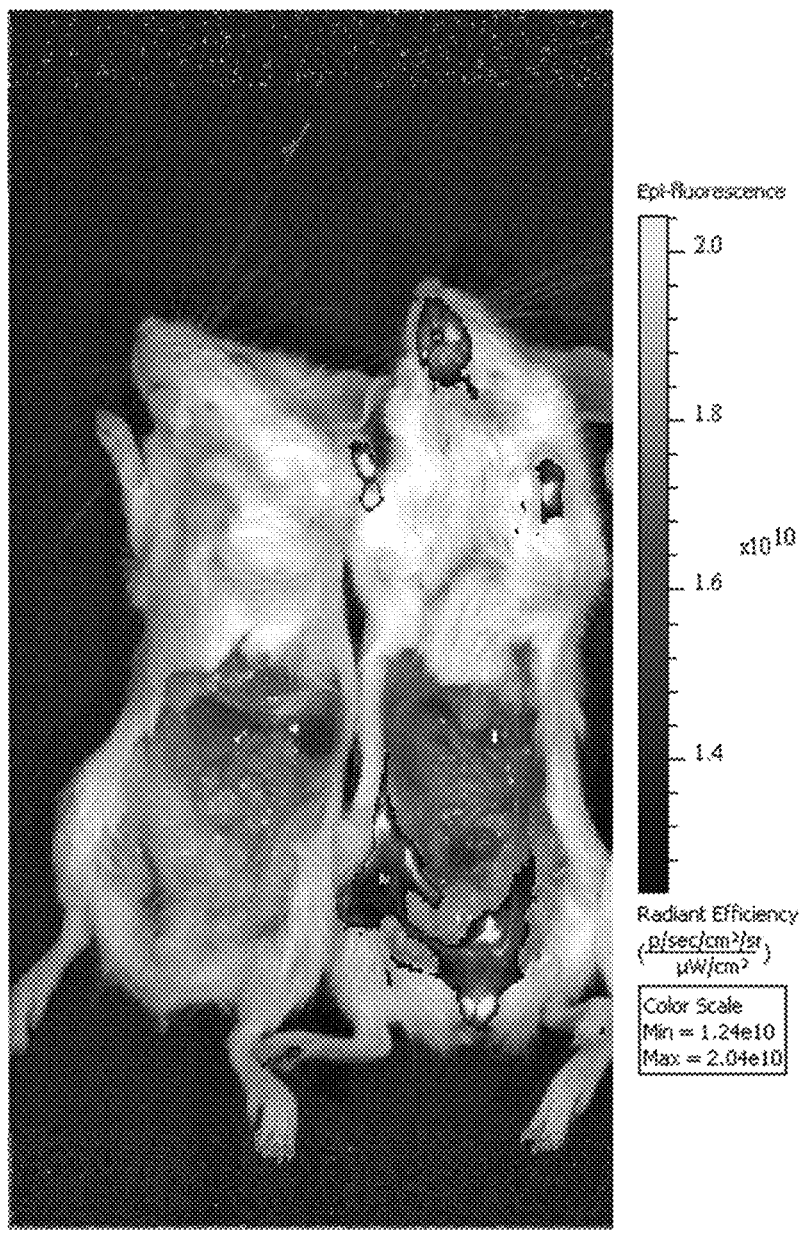
FIG. 1A illustrates a comparison of disease accumulation and disease specificity accumulation and disease specificity after injection of 10 nmol Pte-Tyr-S0456 (OTL-0038) in a healthy mouse (left) and a mouse having ulcerative colitis.

Thus, Applicants have utilized folate-linked compounds potentially capable of altering the function of inflammatory cells, to treat inflammatory cell-mediated disease states.

In another embodiment, the patient may be suffering from a disease state selected from the group consisting of multiple sclerosis, lupus erythematosus, psoriasis and other inflammations of the skin, pulmonary fibrosis, rheumatoid arthritis, atherosclerosis, inflammatory lesions, osteomyelitis, ulcerative colitis, Crohn's disease, organ transplant rejection, fibromyalgia, osteoarthritis, sarcoidosis, systemic sclerosis, Sjogren's syndrome, glomerulonephritis, proliferative retinopathy, restenosis, and chronic inflammation.

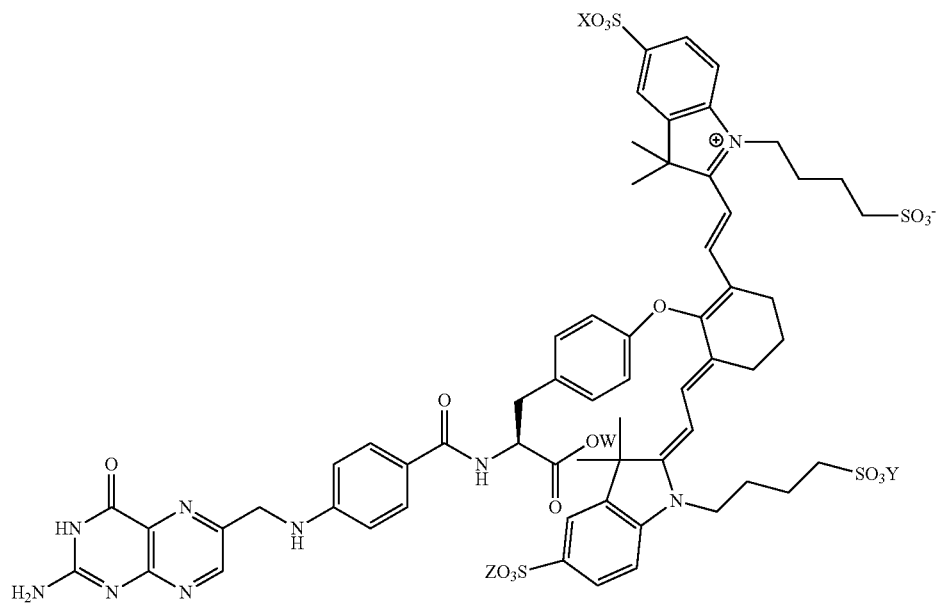

wherein W, X, Y, Z each are H, Na or $NH_4^+$.

The present disclosure provides methods of imaging of inflammatory diseases, including multiple sclerosis, lupus erythematosus, psoriasis, pulmonary fibrosis, and rheumatoid/collagen-induced arthritis (CIA) and diseases in which the immune response contributes to pathogenesis such as atherosclerosis, inflammatory diseases, osteomyelitis, ulcerative colitis, Crohn's disease, graft versus host disease (GVHD), fibromyalgia, osteoarthritis, sarcoidosis, systemic sclerosis, Sjogren's syndrome, inflammations of the skin (e.g., psoriasis), glomerulonephritis, proliferative retinopathy, restenosis, and chronic inflammations, by pteroyl compounds of near infrared dyes that are stable, fluoresce in the infrared range, and penetrate deep within targeted tissue to produce a specific and bright identification of areas of tissue that express folate receptor. More specifically, the pteroyl compounds may be linked to the near infrared dyes through an amino acid linker. Even more specifically, it has been found that where the amino acid linker is tyrosine or a derivative of tyrosine, the intensity of the fluorescence of the dye is maintained or even enhanced.

In preferred embodiments, it is shown herein that such pteroyl compounds specifically bind to folate receptors on for example activated macrophages. Activated macrophages can contribute to the pathophysiology of disease in some instances. Activated macrophages can nonspecifically engulf and kill foreign pathogens within the cells by hydrolytic and oxidative attack resulting in degradation of the pathogen. Peptides from degraded proteins can be displayed on the inflammatory cell surface where they can be recognized by T cells, and they can directly interact with antibodies on the B cell surface, resulting in T and B cell activation and further stimulation of the immune response. Other inflammatory cell types that may be associated with inflammatory disease states include monocytes, and progenitor cells, including endothelial progenitor cells. Such disease states can be imaged by administering to a patient suffering from such disease state an effective amount of a composition comprising a conjugate of the general formula

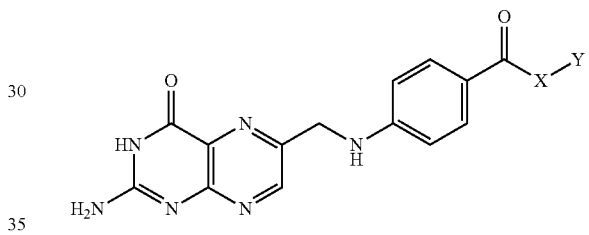

or a pharmaceutically acceptable salt or isotope thereof, wherein X is an amino acid or a derivative thereof, and Y is a dye that has a fluorescence excitation and emission spectra in the near infra red (NIR) range, and the compound maintains or enhances the fluorescence of the dye. Such conjugates, when administered to a patient suffering from inflammation, work to concentrate and associate the conjugated dye with the population of inflammatory cells. Elimination or deactivation of the inflammatory cell population works to stop or reduce the symptoms characteristic of the disease state being treated. Imaging of inflammatory conditions is carried out by local administration of an effective amount of the compound, including administration by injection directly into the body part to be irradiated by the excitation light (e.g., intracavitarily). Conjugate administration is typically continued until symptoms of the disease state are reduced or eliminated.

Moreover, the intensity of the fluorescence is greater than the intensity of previously observed with other near infrared dyes that are targeted with folate for FR isoforms. This increased intensity allows the targeting and clear identification of smaller areas of biological samples (e.g., smaller affected areas of inflammation) from a tissue being monitored. In addition, the increased intensity of the compounds and methods of imaging of the present disclosure provides the added advantage that lower doses/quantities of the dye can be administered and still produces meaningful results. Thus, the methods of imaging of inflammatory diseases with the compounds of the present disclosure lead to more economical imaging techniques. Moreover, there is an added advantaged that a lower dose of the compounds of the disclosure as compared to conventional imaging compounds minimizes the toxicity and other side effects that are attendant with administration of foreign materials to a body.

Furthermore, identification of tissues affected by inflammation will lead to an earlier, more accurate and more effective diagnosis, imaging and identification of satellite disease. Each of these advantages positively correlates with a better clinical outcome for the patient being treated.

In specific experiments, it was found that use of lysine as the linker resulted in loss of near infrared fluorescence. However, it is contemplated that in addition to tyrosine and tyrosine derivatives, a pteroyl compound of a near infrared dye with cysteine or cysteine derivatives also may be useful. Furthermore, it is contemplated that a direct linkage of the pteroyl or folate moiety to the dye or linkage of the dye to pteroic acid or folic acid through an amine linker also produces a loss of intensity of the fluorescence from the compound whereas the presence of the tyrosine or tyrosine derivative as the linking moiety between the pteroyl (targeting moiety) and the near infrared dye (the fluorescing moiety) is beneficial to maintain or enhance the fluorescence of the conjugated compound. Tyrosine-based compounds of the disclosure do not require an extra amine linker to compound the S0456 and further because conjugation through the phenol moiety of the tyrosine leads to enhanced fluorescence.

The compounds can be used with fluorescence-mediated molecular tomographic imaging systems, such as those designed to detect near-infrared fluorescence activation in deep tissues. The compounds provide molecular and tissue specificity, yield high fluorescence contrast, brighter fluorescence signal, and reduce background autofluorescence, allowing for improved early detection and molecular target assessment of diseased tissue in vivo (e.g., cancers or inflammatory disease). The compounds can be used for deep tissue three dimensional imaging, targeted surgery, and methods for quantifying the amount of a target cell type in a biological sample.

Conjugate Compounds

In an aspect the disclosure relates to compounds comprising the formula: Formula (I):

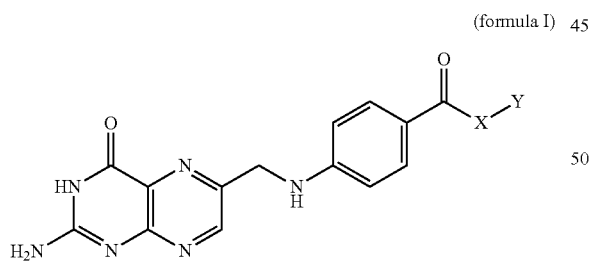

(formula I)

wherein:

X is an amino acid or a derivative thereof, and

Y is a dye that has a fluorescence excitation and emission spectra in the near infra red range, and said compound maintains or enhances the fluorescence of Y.

In some embodiments, the amino acid or amino acid derivative induces a shift in the electronic emission spectrum, the electronic absorption spectrum, or both the electronic emission and absorption spectrum, relative to the electronic spectra of the unmodified dye molecule. Suitably, the shift in the electronic spectrum is a bathochromic shift (i.e., shift to longer wavelength/lower frequency) that helps to improve the detection of the compound in the near infrared (NIR) spectral window and/or reduce the amount of background signal, autofluorescence, interferences from the tissue surrounding the area being visualized. More specifically, this shift in electronic spectrum is particularly observed with NIR dyes that comprise electronegative atoms that are incorporated into the 6-membered ring. Thus, in certain embodiments the amino acid or amino acid (X) derivative comprises an electron-rich moiety such as, for example, oxygen, sulfur, or nitrogen. Non-limiting examples of such amino acids can include cysteine, methionine, threonine, serine, tyrosine, phenylalanine, tryptophan, histidine, lysine, arginine, aspartic acid, glutamic acid, asparagine, and glutamine, or derivatives thereof.

In specific preferred embodiments the disclosure provides a compound of Formula I, wherein Tyr is selected from the group consisting of:

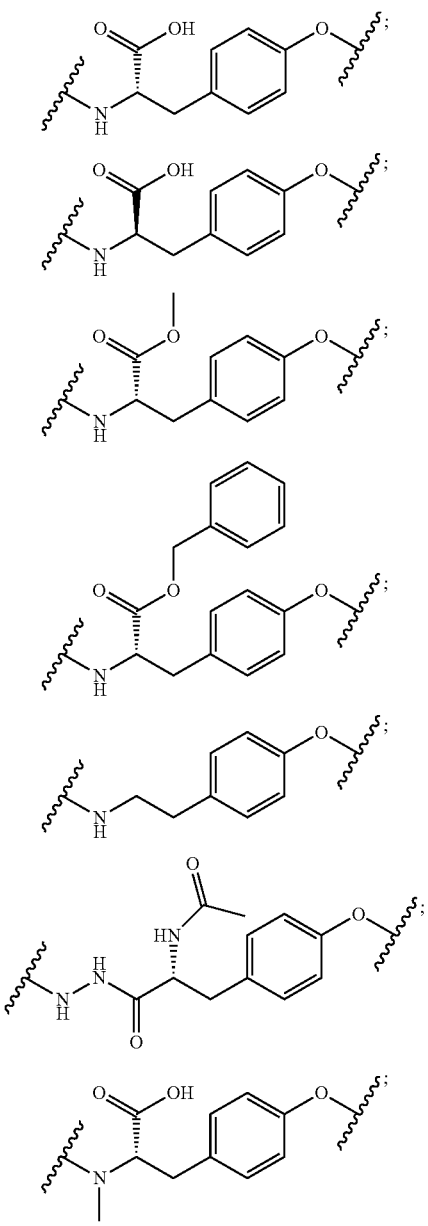

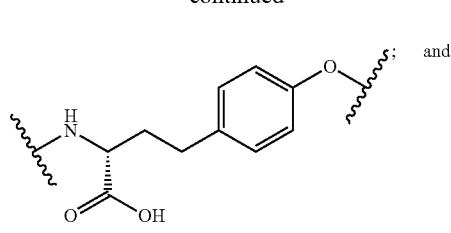

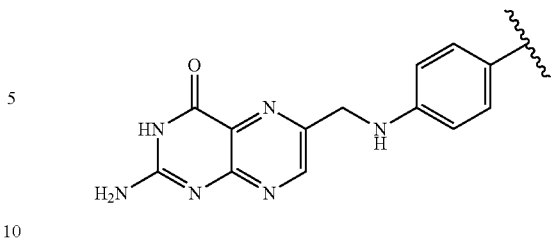

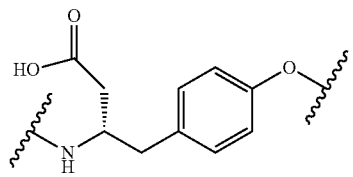

and racemic mixtures and derivatives thereof.

Suitably, the compounds disclosed herein have a maximum light absorption wavelengths in the near infrared region of between about 650 nm and 1000 nm, for example and preferably, at approximately 800 nm.

In specific preferred embodiments, the compounds disclosed herein include a ligand (L) that is effective to target the compound to a particular cell or tissue type and allow for imaging of that targeted cell or tissue. It is preferable the L is either pteroyl moiety or folate moiety and more preferable that L is pteroyl moiety. However, it is contemplated that the skilled person may use some other ligand L to target the compounds to a particular cell surface protein or receptor protein of interest. In specific and preferred embodiments, the ligand comprises pteroyl:

Synthesis of Compounds

The compounds disclosed herein can be made using conventional methods known in the literature. See for example, the dye compounds were synthesized as previously reported.

However, in specific preferred embodiments, the present disclosure provides more efficient synthetic methods for generating the compounds described herein (i.e., Compounds of Formula I), including the compound having the formula

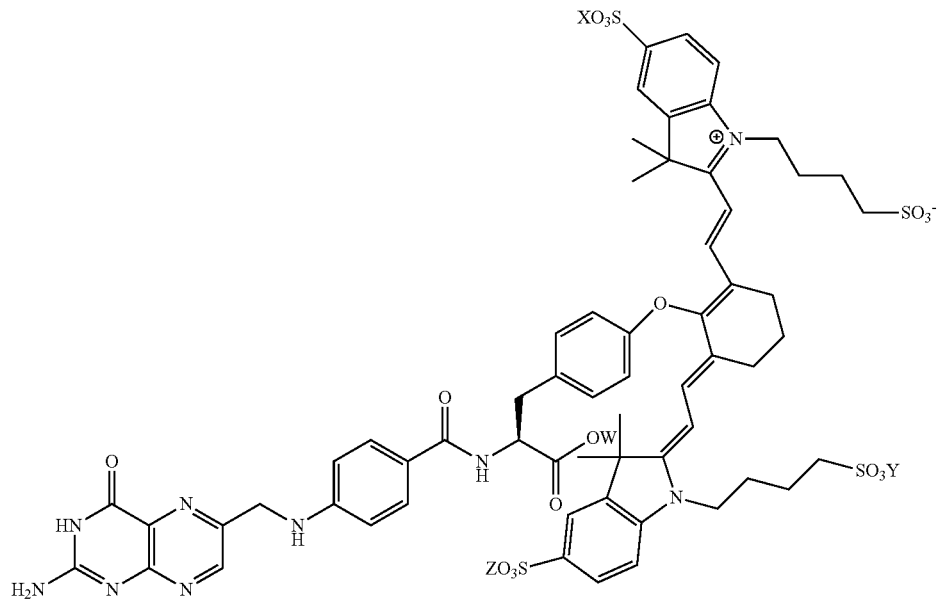

wherein W, X, Y, Z each are H, Na or $NH_4^+$, which can be prepared in accordance to the general schemes outlined in each of Schemes I, II, and III below.

Scheme I, illustrates a synthetic scheme previously used to generate compounds of Formula I where the target ligand comprises an aromatic pterin moiety, such as folate or pteroic acid. The compounds of Formula I where the target ligand comprises folate linked through an amino acid (lysine) to the dye molecule are particularly illustrated by Scheme I. Briefly, the folate ligand modified by attachment to the amino group of the amino acid is reacted with a bridged ether derivative of the dye under conditions to yield products (3) and (4). However, it is notable that compound 3 is the preferred desirably compound but the synthetic pathway lead to presence of undesired by-product 4 as major product that does not have NIR properties. Moreover, its spectral properties are pH dependant. Thus, this scheme demonstrates the major drawback of ether bridged dyes. In the conventional production of these dyes, 30-60% of the yield is of the desired product and whereas 40-70% of the yield is of the undesired byproduct.
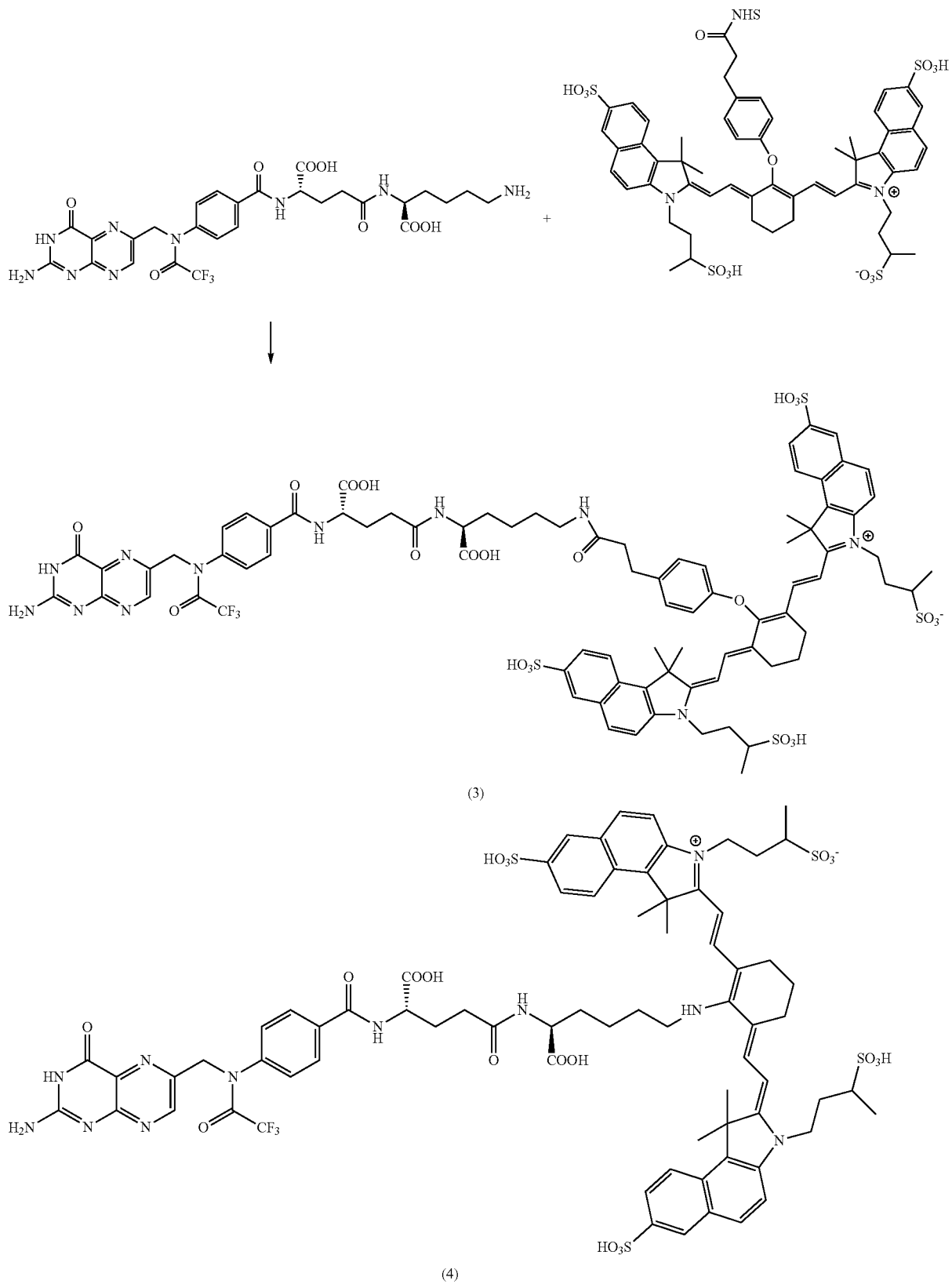

Scheme II provides a synthetic route that includes only three reaction steps and provides the product compound (5) in high yields (above 98%). Briefly, the targeting ligand (1) (illustrated in Scheme II with a pteroyl group) and an amino acid or amino acid derivative (2) that optionally includes protecting groups to avoid undesired reactivity with groups other than the amino group of the amino acid are mixed in a HATU[(O-(7-azabenzotriazol-1-yl)-N,N,N',N'-tetramethyluronium hexafluorophosphate)]/DIPEA (Diisopropylethylamine)/DMF (dimethylformamide) solvent system and reacted at a room temperature and for a sufficient time (5 minutes) to allow coupling of (2) through the amino functionality to ligand (1) to provide (3). Compound (3) can be advantageously precipitated by adding dilute acid to the reaction mixture, including other solvents such as dimethylsulfoxide (DMSO). More specifically, Compound 3 was precipitated in 1N HCl (hydrochloric acid) to get final compound over 98% purity, in these embodiments, the costly HPLC or column chromatography steps are avoided. Compound (3) is reacted to remove the protecting groups on the amino acid portion of the compound by reacting the compound at room temperature in TFA (trifluoroacitic acid):water:TIPS (triisopropylsilane) solvent system for provide compound (4). The compound 4 was purified by precipitation with diethyl ether or methyl-t-butyl ether to yield over 98% purity without HPLC (High performance liquid chromatography) or column chromatography. Compound (4) is reacted in a basic aqueous system (e.g., NaOH, sodium hydroxide) in order to remove the protecting group functionalities and is subsequently reacted, in slight molar excess, with the dye (S0456) in water for a time of 15 minutes and at a temperature of 70-100° C. that allows for coupling between the dye and (4), to yield final compound (5). Compound 5 was precipitated with acetone to give over 98% pure Pte-Tyr-S0456. When NaOH is used the sodium salt of Pte-Tyr-SO456 is produced.

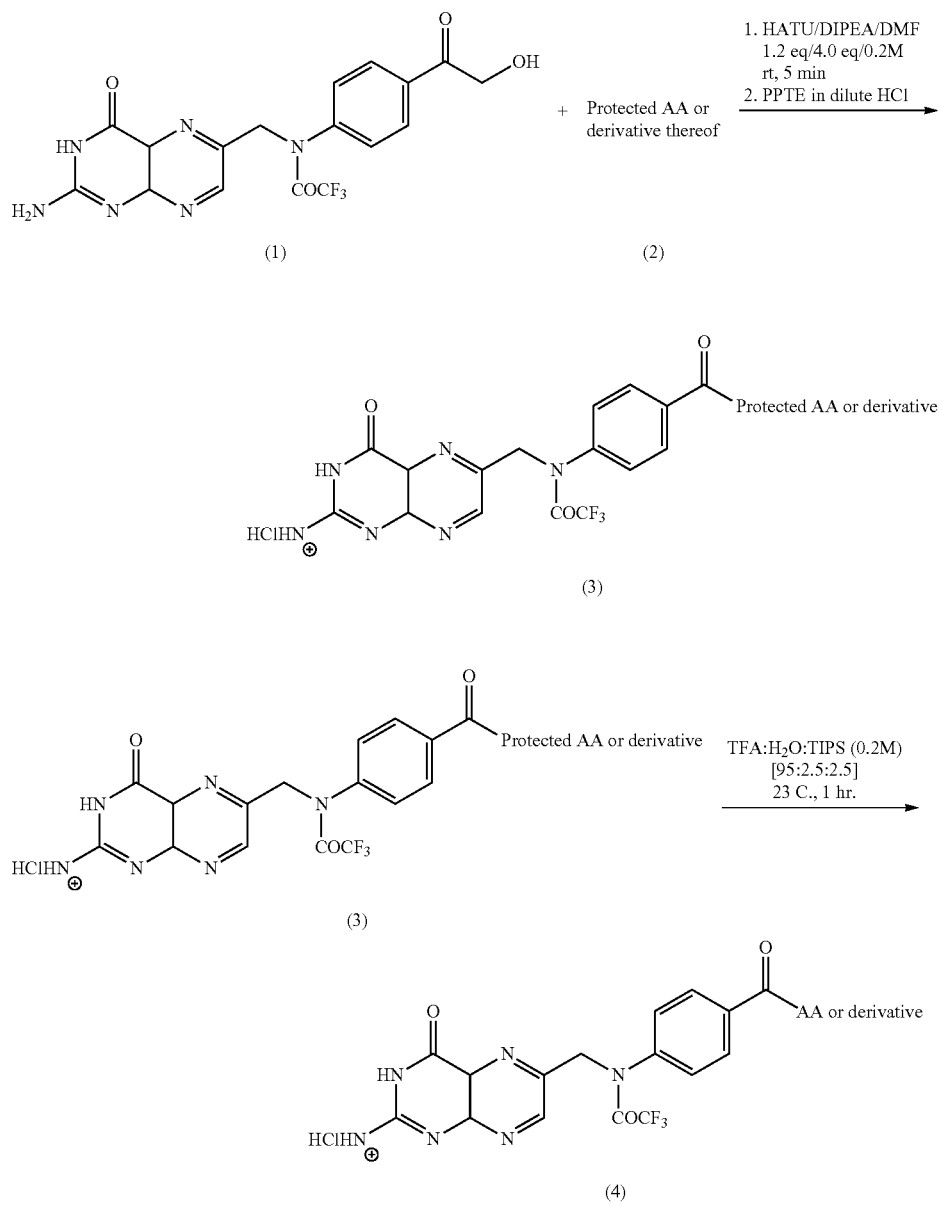

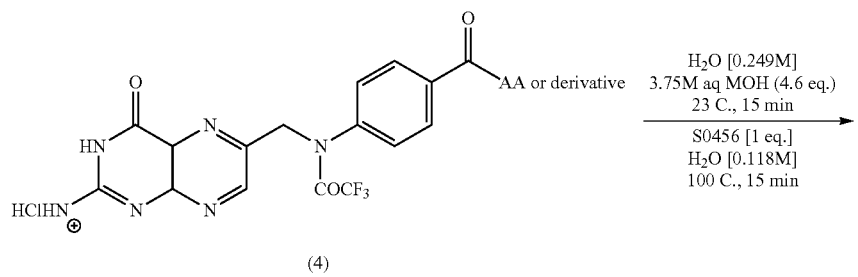

(4)

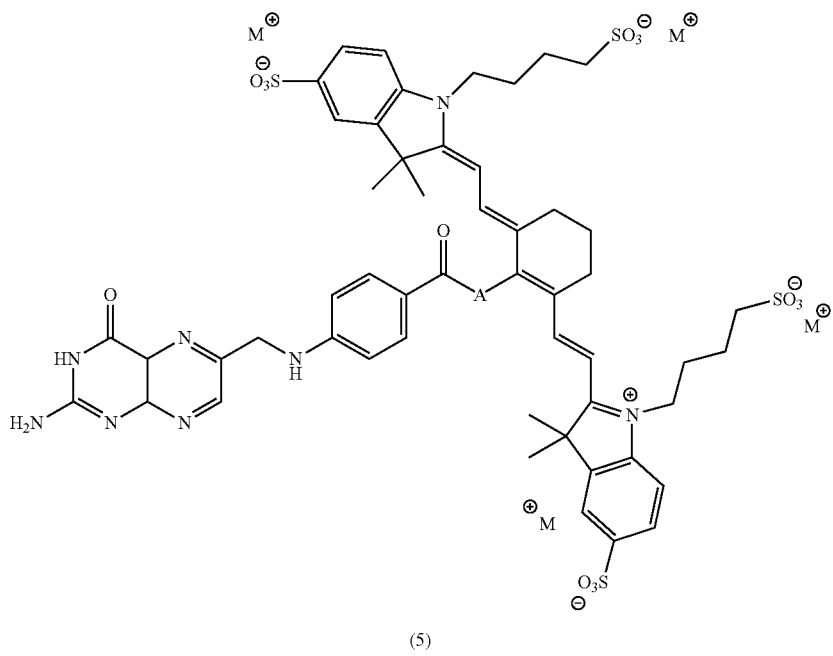

(5)

Scheme III provides an alternative solid phase synthetic route to produce the compounds disclosed herein and provide similar yields as described in Scheme II. Briefly, an amino acid bound to a substrate (1) (illustrated in Scheme III below as protected tyrosine attached to a resin bead) is reacted to remove the Fmoc (Fluorenylmethyloxycarbonyl) protecting group in 20% piperidine in DMF, and is subsequently reacted with the targeting ligand (again illustrated by pteroyl below) in HATU/DIPEA/DMF for a time and at a temperature sufficient to allow coupling of the ligand to the amine functional group of the amino acid to provide (2). Compound (2) is reacted to remove the substrate and any protecting groups on the amino acid in a series of reactions in a TFA:Water:TIPS solvent system to provide (3). Following a similar final step as described in Scheme II, compound (3) is reacted in a basic aqueous system in order to remove the protecting group functionalities and is subsequently reacted, in slight molar excess, with the dye (S0456) in water for a time and at a temperature that allows for coupling between the dye and (3), to yield final compound (4).

Scheme III:

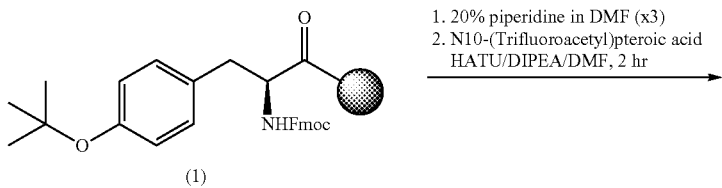

(1)

-continued
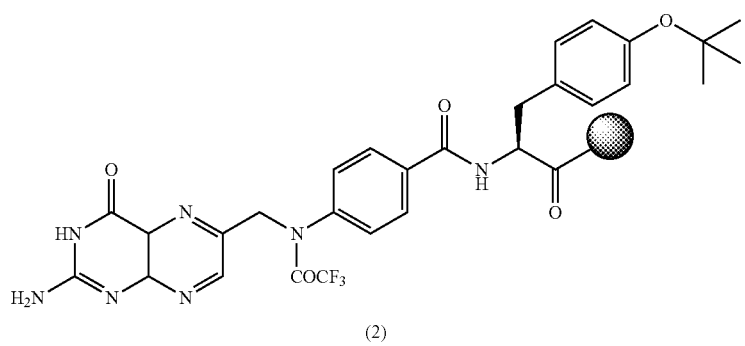
(2)
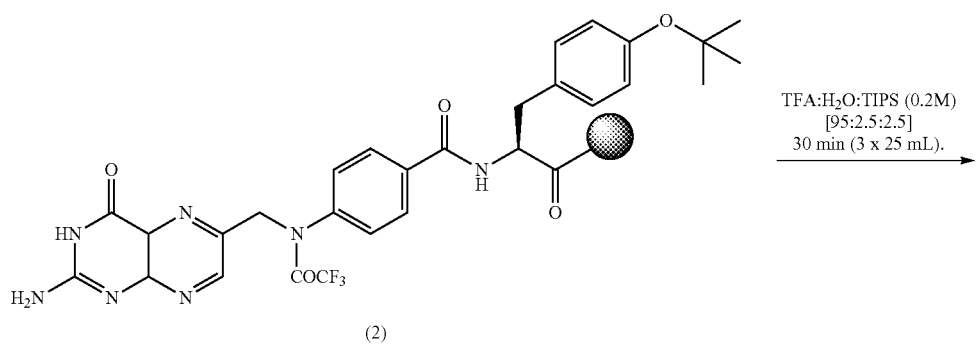
(2) → TFA:H₂O:TIPS (0.2M) [95:2.5:2.5] 30 min (3 x 25 mL).
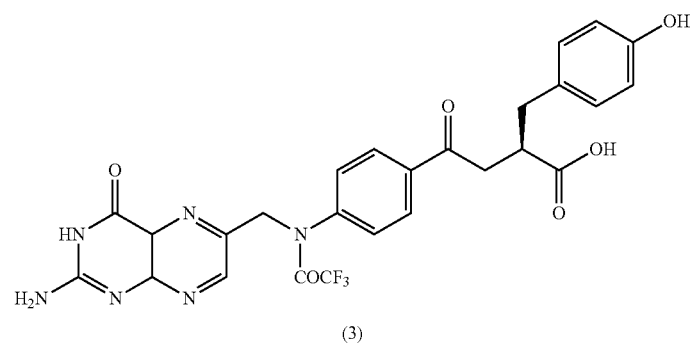
(3)
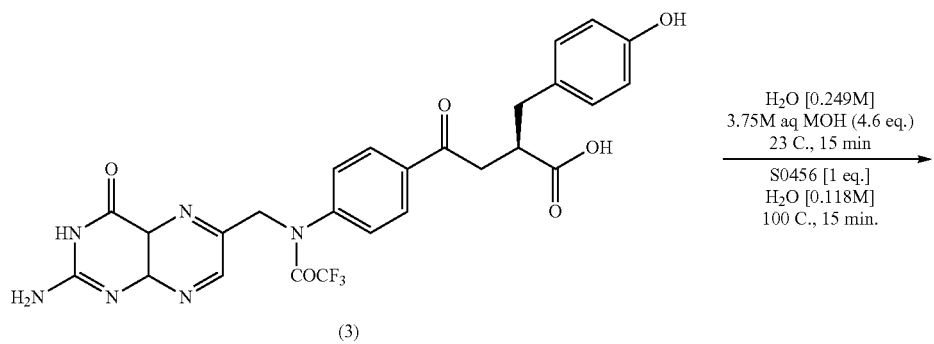
(3) → H₂O [0.249M] 3.75M aq MOH (4.6 eq.) 23 C., 15 min / S0456 [1 eq.] H₂O [0.118M] 100 C., 15 min.

-continued

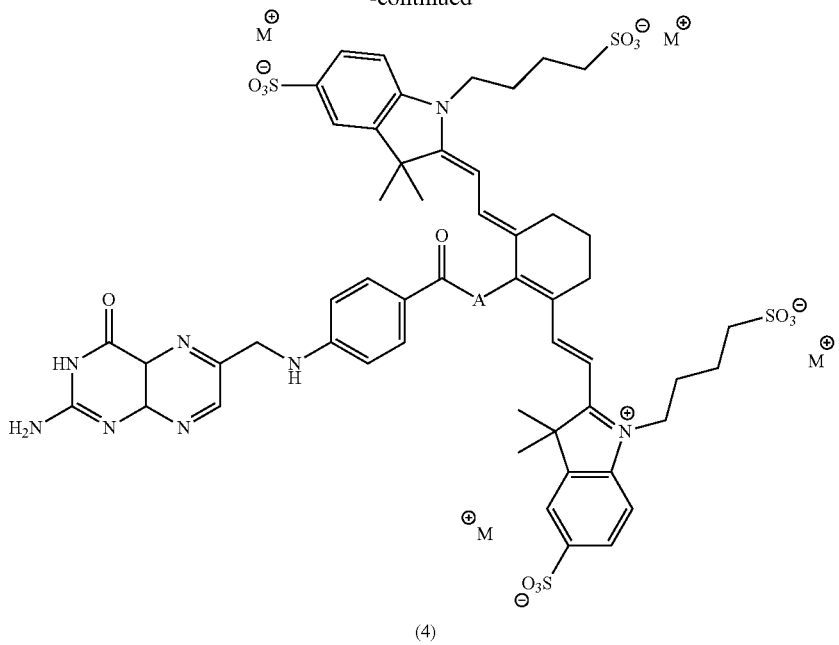

(4)

The above schemes merely illustrate several non-limiting synthetic approaches by which the compounds disclosed herein may be prepared. It will be appreciated that one of skill in the art will be able to identify and incorporate modifications to the above schemes that would provide other compounds having the physical properties that are within the scope of the disclosure. For example, while the above Schemes illustrates folate and pteroyl groups as the targeting ligands of the compounds disclosed herein, one of skill will appreciate that other targeting ligands can be readily incorporated into the synthetic scheme and generate alternative compounds of the Formula I, such as Pte-L-Tyr-S0456 (OTL-0038) as shown in FIG. 1. As another example, a one of skill will appreciate that the absorption/emission wavelengths of the dye portion of the compounds can be modulated by adjusting the length of the polymethine chain and selecting the appropriate aryl or heteroaryl groups (e.g., indole vs. benzindole) as well as linking amino acid groups. In a further example, one of skill in the art will recognize that the extinction coefficient and fluorescence intensity of the dye can be varied by adjusting the rigidity of the polymethine chain (e.g., by introducing a ring system into the polymethine chain such as cyclohexene, cyclobutenone, among others) as is generally known in the art. Accordingly, one of skill in the art will be able to modify the synthesis by selecting the appropriate reagents to make any of the compounds disclosed herein and optionally being able to vary particular physical properties of the compounds.

METHODS OF IMAGING

As noted herein above, there is a need for near infrared dye compounds that specifically target to regions within a tissue. This is so that the compounds may be used in imaging techniques and to assist in the diagnosis and therapeutic intervention of inflammatory disease. As discussed in detail above, the compounds provided herein are useful as dyes and imaging agents in the NIR region of the light spectrum. As such, the compounds have broad applicability to any number of imaging, diagnostic, and targeted therapeutic methods.

In specific embodiments, the present disclosure relates to methods a method of treating an inflammatory disease comprising administering to a patient in need of such a process an effective amount of a compound that incorporate at least one of the compounds disclosed herein (e.g., of Formula I can be used to specifically and sensitively identify inflammatory disease within a tissue. In other embodiments, this disclosure relates to the use of a compound designated Pte-Tyr-S0456 (OTL-0038) for diagnoses and imaging related to image-guided 1) lymph node imaging, 2) inflammatory diseases, 3) atherosclerosis, 4) infection diseases, and/or 5) surgery as well as other uses. In other aspects, the Pte-Tyr-S0456 derivative can be Pte-D-Tyr-S0456, Pte-homo-Tyr-S0456, Pte-β-homo-Tyr-S0456, Pte-(NMe)-Tyr-S0456, Pte-Tyr(OMe)-S0456, Pte-Tyr(OBn)-S0456, Pte-NHNH-Tyr-OAc-S0456, salts, or derivatives thereof. In this manner, the compounds of the present disclosure may be useful in fluorescence guided imaging of systemic inflammation, and if necessary, surgical resection of disease states, lymph nodes, and the like. Alternatively, the compounds of the present disclosure may readily be used in whole body imaging in which the compound is administered to a subject and the localization of the fluorescence facilitates identification of an inflamed tissue or cancer site.

In this manner, the compounds of the present disclosure can be used for the in vivo identification of diseased tissue in a subject in need thereof. The disclosure method includes irradiating an in vivo body part of the subject containing diseased tissue with light having at least one excitation wavelength in the near infrared range from about 600 nm to about 1000 nm. Fluorescence emanating from a compound of the present disclosure administered to the subject and which has specifically bound to and/or been taken up by the diseased tissue in the body part, in response to the at least one excitation wavelength is directly viewed to determine the location and/or surface area of the diseased tissue in the subject.

Light having a wavelength range from 600 nm and 850 nm lies within the near infrared range of the spectrum, in contrast to visible light, which lies within the range from about 400 nm to about 500 nm. Therefore, the excitation light used in practice of the disclosure diagnostic methods will contain at least one wavelength of light to illuminates the tissue at the infrared wavelength to excite the compounds in order that the fluorescence obtained from the area having uptake of the compounds of the present disclosure is clearly visible and distinct from the auto-fluorescence of the surrounding tissue. The excitation light may be monochromatic or polychromatic. In this manner, the compounds of the present disclosure are advantageous as they eliminate the need for use of filtering mechanisms that would be used to obtain a desired diagnostic image if the fluorescent probe is one that fluoresces at wavelengths below about 600 nm. In this manner, the compounds of the present disclosure avoid obscured diagnostic images that are produced as a result of excitation light of wavelengths that would be reflected from healthy tissue and cause loss of resolution of the fluorescent image.

Diagnostic labs, physicians' offices and operating rooms for surgical procedures can be equipped with an overhead light that produces wavelengths of light in the optical emitting spectrum useful in practice of disclosure diagnostic methods, such as lamps that produce light in the appropriate wavelength. Such a light can be utilized in the practice of the disclosure diagnostic methods merely by turning out the other lights in the operating room (to eliminate extraneous light that would be visibly reflected from tissue in the body part under investigation) and shining the excitation light of near infrared wavelength into the body cavity or surgically created opening so that the fluorescent image received directly by the eye of the observer (e.g., the surgeon) is predominantly the fluorescent image emanating from the fluorophore(s) in the field of vision. Light emanating from a source in the 600 nm and 850 nm range, preferably 750 nm-850 nm range would be used in accomplishing the goal of direct visualization by the observer so that light reflecting from the body part, other than that from the fluorescing moiet(ies), is minimized or eliminated.

Accordingly, the diseased tissue (and bound or taken-up targeting construct) is "exposed" to the excitation light (e.g., by surgically created opening or endoscopic delivery of the light to an interior location. The disclosure of these methods of imaging is particularly suited to in vivo detection of diseased tissue located at an interior site in the subject, such as within a natural body cavity or a surgically created opening, where the diseased tissue is "in plain view" (i.e., exposed to the human eye) to facilitate a procedure of biopsy or surgical excision of the area that has been highlighted by uptake of the compounds of the present disclosure. As the precise location and/or surface area of the diseased or inflamed tissue are readily determined by the uptake of the compounds of the present disclosure, the methods employing the compounds of the present disclosure provide a valuable guide to pathologists, immunologists, technicians and surgeons alike, who needs to "see" in real time the exact outlines, size, etc. of the mass of the inflamed areas for diagnosis and imaging, and if necessary, surgery.

Thus, in specific embodiments, the present disclosure entails optical imaging of a biological tissue that expresses a folate receptor through administration to a patient having an inflammatory disease by contacting the tissue with a composition comprising an effective amount of compounds of the present disclosure (e.g., compounds of Formula I) and allowing time for the compound in the composition to distribute within the tissue and interact with the site of folate receptor. After a sufficient time for such interaction has passed, the tissue is illuminated with an excitation light to cause the compound in the composition to fluoresce. The fluorescence is then detected as and where such fluorescence is observed is an area that contains the folate receptor.

In like manner, the compounds of the present disclosure are used to identify a target cell type in a biological sample by contacting the biological sample with such compounds for a time and under conditions that allow for binding of the compound to at least one cell of the target cell type. The bound compound is then optically detected such that presence of fluorescence of the near infrared wavelength emanating from the bound, targeted compound of the present disclosure indicated that the target cell type is present in the biological sample. This method thus provides an image of the targeted cell type in the tissue being assessed. Most preferably, the targeted cell type is an activated inflammatory cell, including but not limited to macrophages, monocytes, and progenitor cells, including endothelial progenitor cells.

The most suitable route for administration of an effective amount of the conjugated compounds disclosed herein will vary depending upon the disease state to be treated, or the location of the suspected condition to be diagnosed. This includes but is not limited to parentally, e.g., intradermally, subcutaneously, intramuscularly, intraperitoneally, or intravenously. In other embodiments, the conjugate may be administered to the patient by other medically useful processes, and any effective dose and suitable therapeutic dosage form, including prolonged release dosage forms, can be used. Illustratively, the method described herein may be used in combination with biological therapies such as other immunotherapies including, but not limited to, monoclonal antibody therapy, treatment with immunomodulatory agents, and vaccination. For example, for treatment of inflammatory conditions, local administration, including administration by injection directly into the body part to be irradiated by the excitation light (e.g., intracavitarily) provides the advantage that the targeting construct (e.g., fluorescently tagged antibodies) can be administered in a high concentration without risk of the complications that may accompany systemic administration thereof. However, oral, topical and parenteral applications can also be envisioned.

These methods advantageously provide an improved method of performing image-guided diagnosis and treatment of inflammatory disease on a subject as the administration of a composition comprising the compound of the disclosure under conditions and for a time sufficient for said compound to accumulate at a given tissue site will assist a physician in visualizing the tissue to be treated.

If the putative diseased site is a natural body cavity or surgically produced interior site, an endoscopic device can be optionally used to deliver the excitation light to the site, to receive fluorescence emanating from the site within a body cavity, and to aid in formation of a direct image of the fluorescence from the diseased tissue. For example, a lens in the endoscopic device can be used to focus the detected fluorescence as an aid in formation of the image. As used herein, such endoscope-delivered fluorescence is said to be "directly viewed" by the practitioner and the tissue to which the targeting construct binds or in which it is taken up must be "in plain view" to the endoscope since the light used in the disclosure diagnostic procedure will not contain wavelengths of light that penetrate tissue, such as wavelengths in the near infrared range. Alternatively, the excitation light may be directed by any convenient means into a body cavity or surgical opening containing a targeting construct administered as described herein and the fluorescent image so produced can be directly visualized by the eye of the observer without aid from an endoscope. With or without aid from any type of endoscopic device, the fluorescent image produced by the disclosure method is such that it can be viewed without aid of an image processing device, such as a CCD camera, TV monitor, photon collecting device, and the like.

It is contemplated that the diagnostic or imaging methods of the present disclosure allow the surgeon/practitioner to contemporaneously see/view/visualize diseased or abnormal tissue through a surgical opening to facilitate a procedure of biopsy or surgical excision. As the location and/or surface area of the diseased tissue are readily determined by the diagnostic procedure of the disclosure employing the compounds described herein, the disclosure method is a valuable guide to the surgeon, who needs to know the exact outlines, size, etc. of the mass, for example, for resection as the surgery proceeds. In particular, it is noted that the compounds of the disclosure fluorescence in the near infrared range to a greater intensity than those previously described. As such, advantageously, it is contemplated that less of the compound will be needed to achieve diagnostic imaging. In addition, the compounds of the present disclosure penetrate deep into the tissue and hence the disclosure advantageously allows a greater accuracy that the proper course of treatment of the inflammatory disease is taken.

In some embodiments, a single type of fluorescent moiety is relied upon for generating fluorescence emanating from the irradiated body part (i.e., from the fluorescent targeting construct that binds to or is taken up by diseased tissue) and subjecting the targeting construct with a source of light from the near infrared spectrum.

In other embodiments, it is contemplated that a plurality. (i.e., two, three, four, or more) targeting constructs are used to obtain a diagnostic image. Such additional targeting constructs may be additional compounds of the present disclosure distinct from the first such compound. Alternatively, the additional targeting constructs may comprise the dyes described herein but with the pteroyl moiety being replaced by a ligand for another receptor other than folate receptor. In still other embodiments, the additional targeting moieties may be other fluorescing targeting constructs (e.g., antibodies, or biologically active fragments thereof, having attached fluorophores) that bind to other receptors or antigens on the tumor or tissue (e.g., a site of atherosclerosis, infection, cardiovascular diseases, neurodegenerative diseases, immunologic diseases, autoimmune diseases, respiratory diseases, metabolic diseases, inherited diseases, infectious diseases, bone diseases, and environmental diseases or the like) to be imaged. Any additional targeting moiety that specifically targets the tumor or specific site on the tissue may be used provided that it is specific for the site to be monitored. The purpose of the additional fluorescing targeting construct is to increase the intensity of fluorescence at the site to be monitored thereby aiding in detection of diseased or abnormal tissue in the body part. For example, a given diseased tissue may have numerous markers and in addition to the compounds of the present disclosure a cocktail of fluorescent moieties is provided which are specific for that given site such that the signal emanating from the tissue is generated by more than one compound or fluorescent moiety that has targeted and become localized to the tissue site of interest.

In practice, the skilled person would administer a compound of the present disclosure either alone or as part of a cocktail of targeting detectable moieties and allow these compounds and targeting moieties to bind to and/or be taken up by any targeting tissue that may be present at the site under investigation and then provide a supply of the light source. Typically, the compounds of the present disclosure and any additional targeting moieties will be administered prior to surgery for a time and in compositions that allow the fluorescent compounds of the present disclosure as well as any additional fluorescent constructs to be taken up by the target tissue.

Those of skill in the art will be able to devise combinations of successively administered fluorescing targeting constructs, each of which specifically binds to the target site. It is preferable that all of the fluorescing targeting constructs used in such cocktails to identify the target tissue comprise fluorophores that fluoresce within the same wavelength band or at the same wave length as does the compound of the present disclosure (e.g. a fluorescing sensitive to near infrared wavelength of light in the compounds of the present disclosure) to minimize the number of different light sources that need to be employed to excite simultaneous fluorescence from all of the different targeting constructs used in practice of the disclosure method. However, it is contemplated that the additional targeting moieties other than the compounds of the present disclosure may fluorescence in response to the irradiating light at a different color (i.e., has a different wavelength) than that from the florescent compounds of the present disclosure. The difference in the colors of the fluorescence emanating from the compounds of the present disclosure and those of the additional targeting compounds may aid the observer in determining the location and size of the diseased tissue. In some examples, it may be desirable to include fluorophores in targeting constructs targeted to target normal tissue and the compounds of the present disclosure to target diseased tissue such that the contrast between the diseased tissue and normal tissue is further enhanced to further aid the observer in determining the location and size of the target tissue. The use of such additional fluorophores and targeting agents in addition to the compounds of the present disclosure provides the advantage that any natural fluorescence emanating from normal tissue is obscured by the fluorescence emanating from fluorophore(s) in supplemental targeting constructs targeted to the normal tissue in the body part. The greater the difference in color between the fluorescence emanating from normal and target tissue, the easier it is for the observer to visualize the outlines and size of the target tissue. For instance, targeting a fluorescing targeting construct comprising a fluorophore producing infrared light from the compounds of the present disclosure to the target tissue (i.e., abnormal tissue) and a fluorophore producing green light to healthy tissue aids the observer in distinguishing the target tissue from the normal tissue. Those of skill in the art can readily select a combination of fluorophores that present a distinct visual color contrast.

The spectrum of light used in the practice of the disclosure method is selected to contain at least one wavelength that corresponds to the predominate excitation wavelength of the targeting construct, or of a biologically compatible fluorescing moiety contained within the targeting construct. Generally the excitation light used in practice of the disclosure method comprises at least one excitation wavelength of light in the near infrared wavelength range from about 600 nm to about 850 nm However, when a combination of targeting ligands that fluoresce at different wavelengths is used in practice of the disclosure, the spectrum of the excitation light must be broad enough to provide at least one excitation wavelength for each of the fluorophores used. For example, it is particularly beneficial when fluorophores of different colors are selected to distinguish normal from diseased tissue, that the excitation spectrum of the light(s) include excitation wavelengths for the fluorophores targeted to normal and target tissue.

As noted herein the compounds of the present disclosure are specifically targeted to the folate receptor by way of pteroyl or folate ligand being part of the compounds of the present disclosure. In embodiments where an additional targeting moiety is used, the targeting construct of such an additional targeting moiety is selected to bind to and/or be taken up specifically by the target tissue of interest, for example to an antigen or other surface feature contained on or within a cell that characterizes a disease or abnormal state in the target tissue. As in other diagnostic assays, it is desirable for the targeting construct to bind to or be taken up by the target tissue selectively or to an antigen associated with the disease or abnormal state; however, targeting constructs containing ligand moieties that also bind to or are taken up by healthy tissue or cell structures can be used in the practice of the disclosure method so long as the concentration of the antigen in the target tissue or the affinity of the targeting construct for the target tissue is sufficiently greater than for healthy tissue in the field of vision so that a fluorescent image representing the target tissue can be clearly visualized as distinct from any fluorescence coming from healthy tissue or structures in the field of vision.

The disease or abnormal state detected by the disclosure method can be any type characterized by the presence of a known target tissue for which a specific binding ligand is known. For example, various heart conditions are characterized by production of necrotic or ischemic tissue or production of artherosclerotic tissue for which specific binding ligands are known. It is contemplated that the target tissue may be characterized by cells that produce either a surface antigen for which a binding ligand is known, or an intracellular marker (i.e. antigen), since many targeting constructs penetrate the cell membrane. Representative disease states that can be identified using the disclosure method include such various conditions as different types of tumors, bacterial, fungal and viral infections, and the like. As used herein "abnormal" tissue includes precancerous conditions, necrotic or ischemic tissue, and tissue associated with connective tissue diseases, and auto-immune disorders, and the like. Further, examples of the types of target tissue suitable for diagnosis or examination using the disclosure method include cardiac, breast, ovarian, uterine, lung, endothelial, vascular, gastrointestinal, colorectal, prostatic tissue, endocrine tissue, and the like, as well as combinations of any two or more thereof.

Simply by way of example, antigens for some common malignancies and the body locations in which they are commonly found are known to those of skill in the art, and targeting ligands, such as antibodies or for these antigens or indeed ligands where the antigens are receptors are known in the art.

The targeting constructs and supplemental targeting constructs used in practice of the disclosure method can be administered by any route known to those of skill in the art, such as topically, intraarticularly, intracisternally, intraocularly, intraventricularly, intrathecally, intravenously, intramuscularly, intraperitoneally, intradermally, intratracheally, intracavitarily, and the like, as well as by any combination of any two or more thereof.

The most suitable route for administration will vary depending upon the disease state to be treated, or the location of the suspected condition or tumor to be diagnosed. For example, for imaging of inflammatory conditions and various tumors, local administration, including administration by injection directly into the body part to be irradiated by the excitation light (e.g., intracavitarily) provides the advantage that the targeting construct (e.g., fluorescently tagged antibodies) can be administered in a high concentration without risk of the complications that may accompany systemic administration thereof.

The compounds of the present disclosure as well as any additional targeting constructs used in diagnostic cocktails comprising the compounds of the present disclosure are administered in a "effective amount" for diagnosis. An effective amount is the quantity of a targeting construct necessary to aid in direct visualization of any target tissue located in the body part under investigation in a subject. A "subject" as the term is used herein is contemplated to include any mammal, such as a domesticated pet, farm animal, or zoo animal, but preferably is a human. Amounts effective for diagnostic use will, of course, depend on the size and location of the body part to be investigated, the affinity of the targeting construct for the target tissue, the type of target tissue, as well as the route of administration. Local administration of the targeting construct will typically require a smaller dosage than any mode of systemic administration, although the local concentration of the targeting construct may, in some cases, be higher following local administration than can be achieved with safety upon systemic administration.

An effective amount of the conjugate compound to be administered will be dependent on the patient's condition, the disease state being treated, the molecular weight of the conjugate, its route of administration and tissue distribution, and the possibility of co-usage with therapeutic treatments such as radiation therapy. The effective amount to be administered to a patient is based on body surface area, patient weight, and physician assessment of patient condition. In various exemplary embodiments, an effective dose amount may be done with or without an excipient/carrier, including but not limited to saline. Since individual subjects may present a wide variation in severity of symptoms and each targeting construct has its unique diagnostic characteristics, including, affinity of the targeting construct for the target, rate of clearance of the targeting construct by bodily processes, the properties of the fluorophore contained therein, and the like, the skilled practitioner will weigh the factors and vary the dosages accordingly.

The compounds of the present disclosure as well as cocktails comprising these compounds can be formulated as a sterile injectable suspension according to known methods using suitable dispersing or wetting agents and suspending agents. The sterile injectable preparation may also be a sterile injectable solution or suspension in a non-toxic parenterally-acceptable diluent or solvent, for example, as a solution in 1-4, butanediol. Sterile, fixed oils are conventionally employed as a solvent or suspending medium. For this purpose any bland fixed oil may be employed, including synthetic mono- or diglycerides, fatty acids (including oleic acid), naturally occurring vegetable oils like sesame oil, coconut oil, peanut oil, cottonseed oil, etc., or synthetic fatty vehicles like ethyl oleate, or the like. Buffers, preservatives, antioxidants, and the like, can be incorporated as required, or, alternatively, can comprise the formulation.

The examples that follow are merely provided for the purpose of illustrating particular embodiments of the disclosure and are not intended to be limiting to the scope of the appended claims. As discussed herein, particular features of the disclosed compounds and methods can be modified in various ways that are not necessary to the operability or advantages they provide. For example, the compounds can incorporate a variety of amino acids and amino acid derivatives as well as targeting ligands depending on the particular use for which the compound will be employed. One of skill in the art will appreciate that such modifications are encompassed within the scope of the appended claims.

EXAMPLES

Example 1

In Vivo Studies of Ulcerative Colitis with Pte_L_Tyr_S0456 (OTL-0038)

Seven weeks old Balb/c mice (Harlan Laboratories) maintained on a folate-deficient diet were administered 5% dextran sodium sulfate (DSS) in their drinking water to induce ulcerative colitis. Healthy control mice received normal drinking water.

Figure 1B:
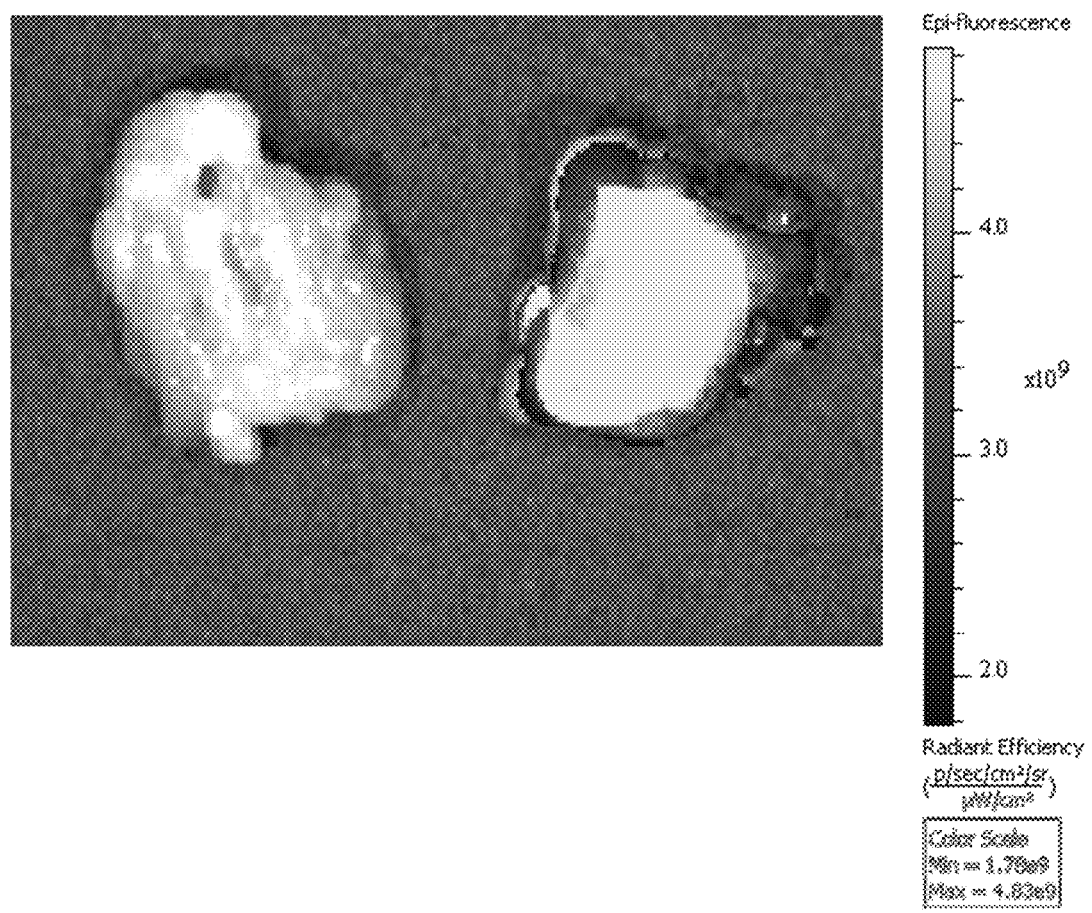
FIG. 1B illustrates a comparison of disease accumulation and disease specificity in the whole gastrointestinal tract including small and large intestine after injection of 10 nmol Pte-Tyr-50456 (OTL-0038) in a healthy mouse (left) and a mouse having ulcerative colitis.
Figure 1C:
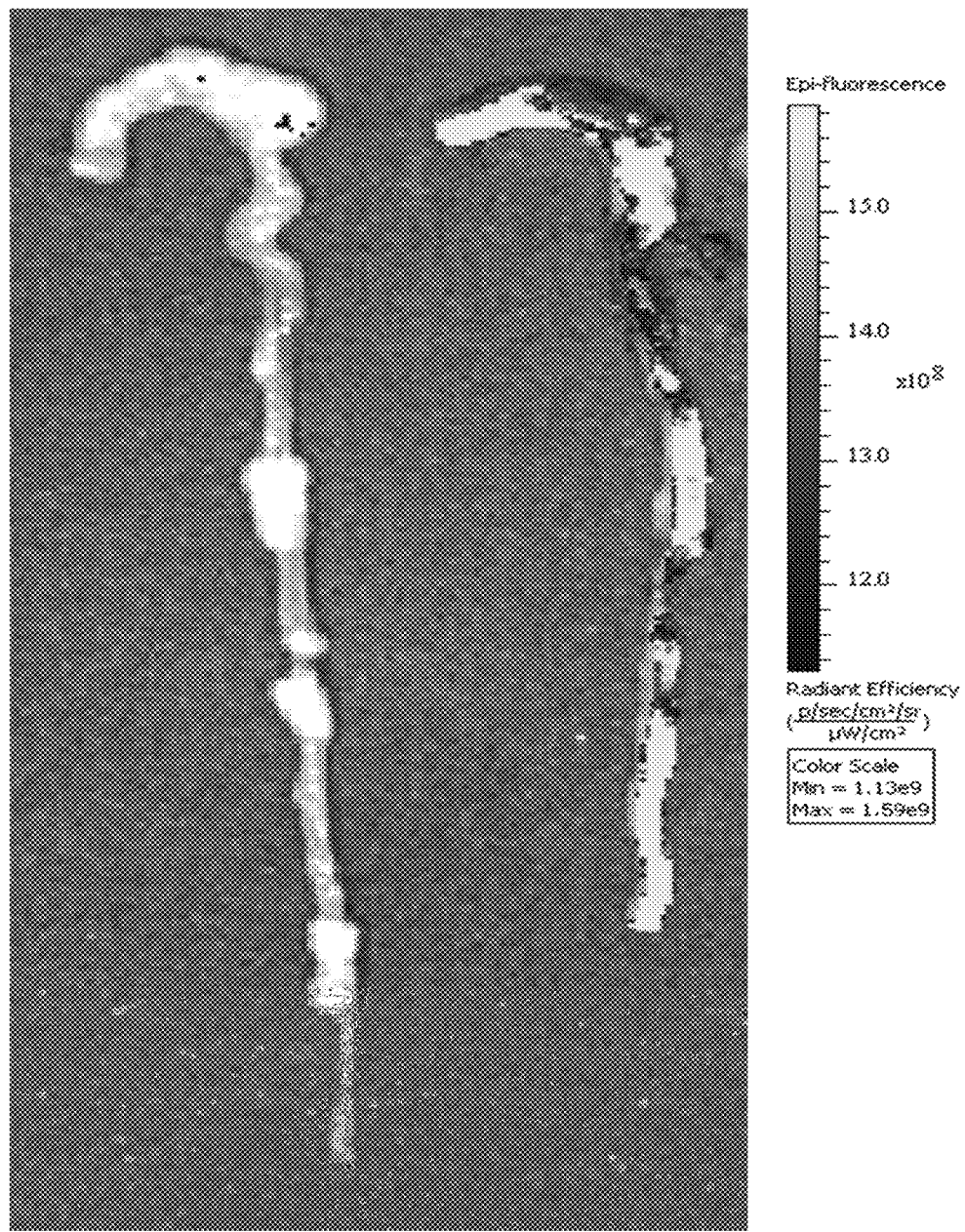
FIG. 1C illustrates a comparison of disease accumulation and disease specificity in the large intestine after injection of 10 nmol Pte-Tyr-S0456 (OTL-0038) in a healthy mouse (left) and a mouse having ulcerative colitis.

After 8 days, mice were intraperitoneally injected with 10 nmol OTL-0038. After 4 hours, the mice were euthanized and imaged using an IVIS lumina II (as shown in FIGS. 1A-C).

Example 2

In Vivo Studies of Collagen-Induced Arthritis (CIA) (as a Model for Rheumatoid Arthritis) with Pte_L_Tyr_S0456 (OTL-0038)

6-7 weeks old female DBA/1 mice (Jackson Laboratories) were maintained on folate-deficient diet (Harlan-Teklad). Mice were immunized at the base of the tail with 100 µg bovine type II collagen emulsified in complete Freund's adjuvant (Chondrex, Inc., Redmond, Wash., USA). Mice were then boosted 21 days later with a similar injection of 100 µg bovine type II collagen emulsified in incomplete Freund's adjuvant. After four days (Day 25), onset of arthritis was synchronized in all mice with an intraperitoneal injection of 25 µg lipopolysaccharide (LPS) dissolved in saline. Healthy control mice did not undergo arthritis induction.

Figure 2A:
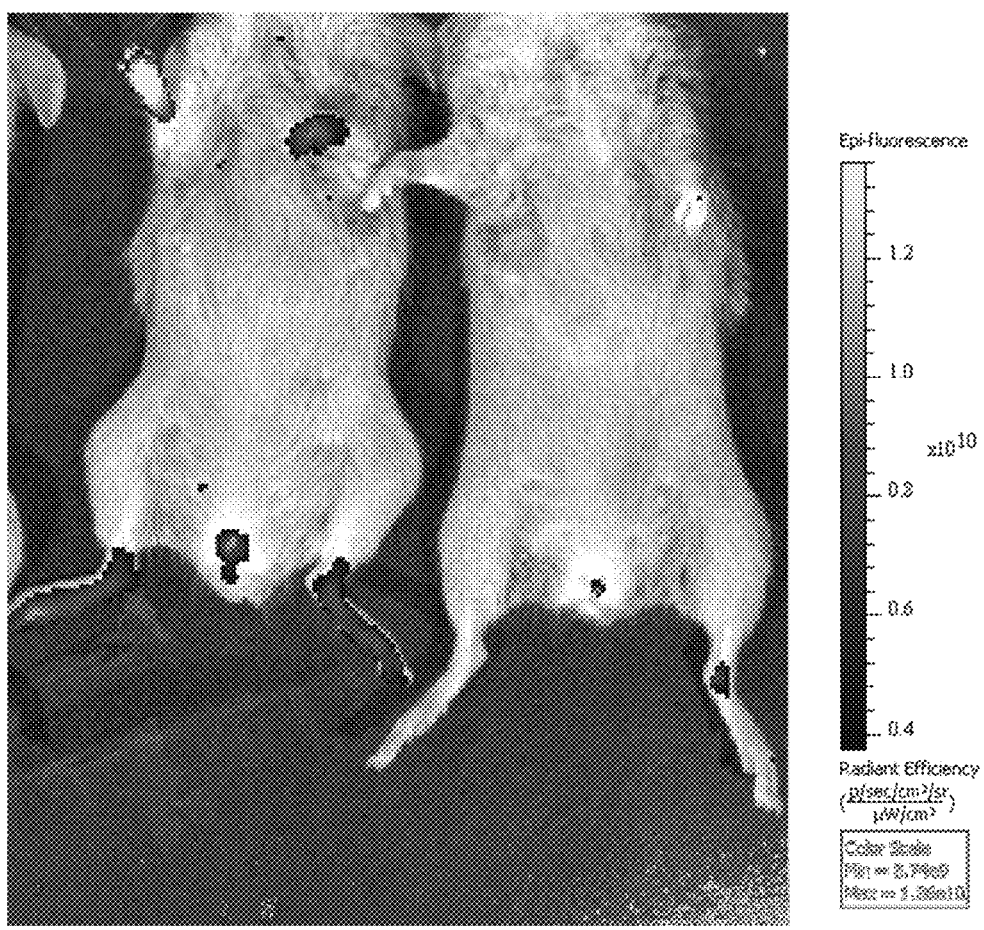
FIG. 2A illustrates a comparison of disease accumulation and disease specificity after injection of 10 nmol Pte-Tyr-S0456 (OTL-0038) in a healthy mouse (right) and a diseased mouse having collagen-induced arthritis (CIA) (left).
Figure 2B:
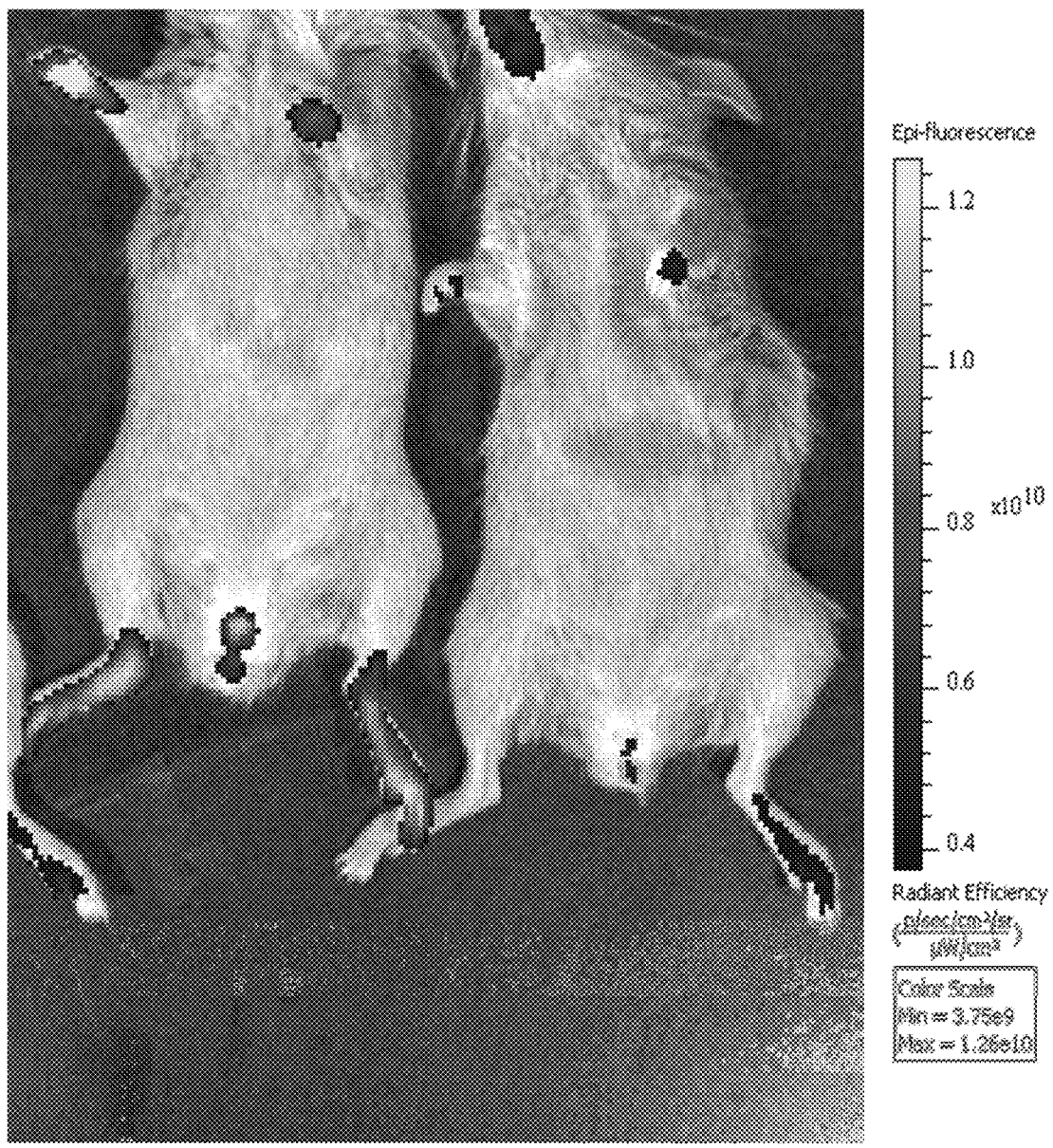
FIG. 2B illustrates a comparison of disease accumulation and disease specificity after injection of 10 nmol Pte-Tyr-S0456 (OTL-0038) in a healthy mouse and a mouse having collagen-induced arthritis (CIA).

On Day 39, mice received an intraperitoneal injection of 10 nmol OTL-0038. After 4 hours, mice were euthanized and imaged on an IVIS lumina II (as shown in FIGS. 2A-2B).

Example 3

In Vivo Studies of Atherosclerosis with Pte_L_Tyr_S0456 (OTL-0038)

Five weeks old male ApoE−/− mice were purchased from Jackson Laboratories and placed on an adjusted calorie diet (42% from fat, Harlan Laboratories). Healthy control mice were maintained on normal chow.

Figure 3A:
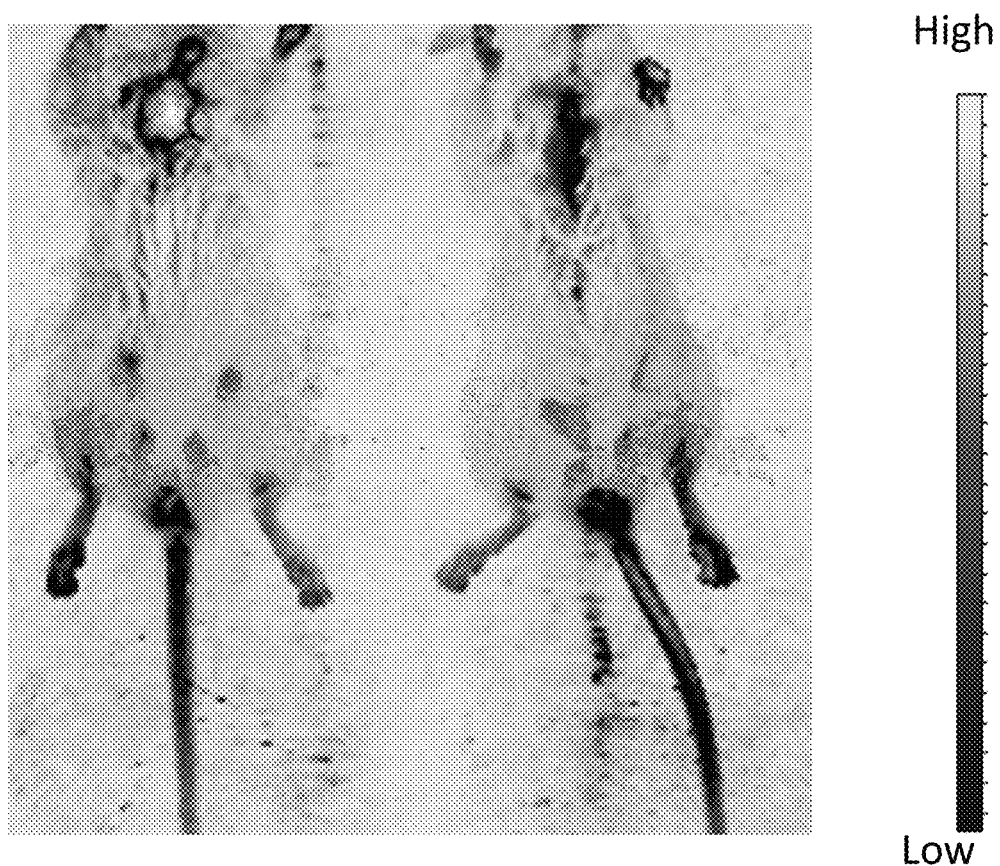
FIG. 3A illustrates a comparison of disease accumulation and disease specificity after injection of 10 nmol Pte-Tyr-SO456 (OTL-0038) in a healthy mouse (right) and a mouse having atherosclerosis (left).
Figure 3B:
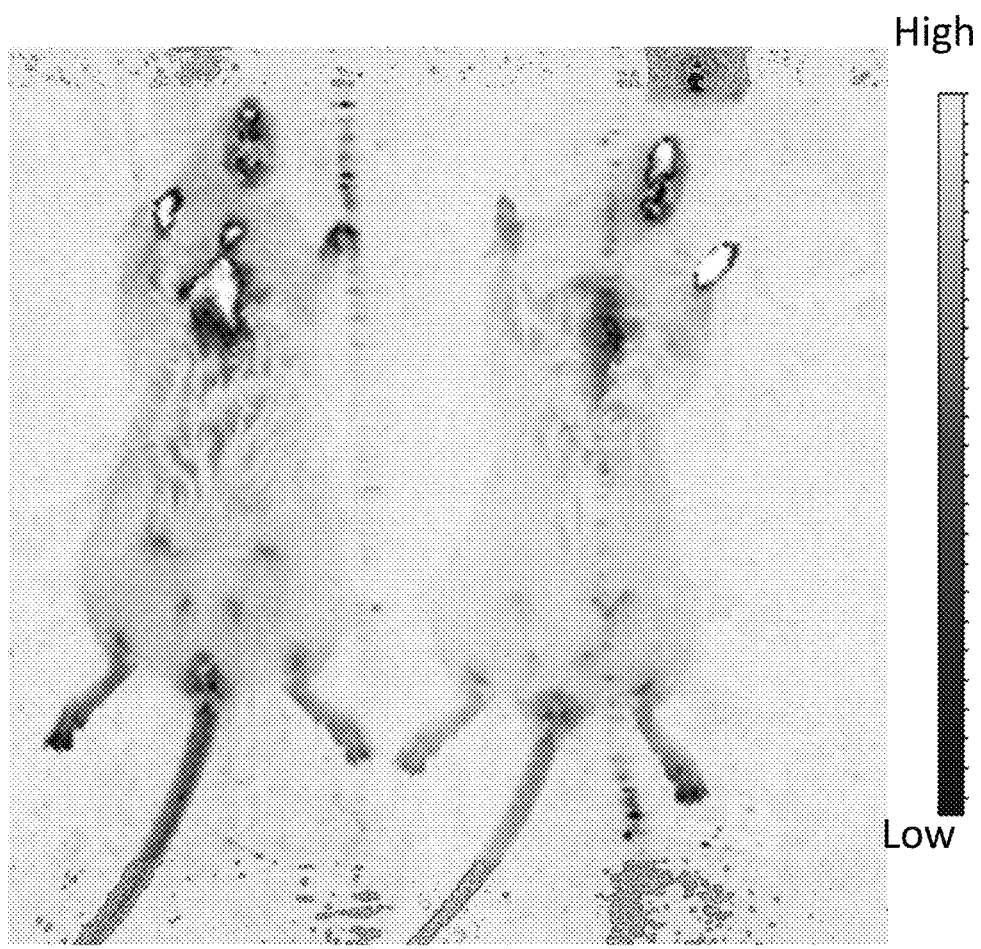
FIG. 3B illustrates a comparison of disease accumulation and disease specificity after injection of 10 nmol Pte-Tyr-S0456 (OTL-0038) in a healthy mouse (right) and a mouse having atherosclerosis (left).

After 20 weeks, mice received an i.p. injection of 10 nmol OTL38. After 4 hours, mice were euthanized and imaged on an IVIS lumina II (as shown in FIGS. 3A-3B).

Example 4

In Vivo Studies of Pulmonary Fibrosis with Pte_L_Tyr_S0456 (OTL-0038)

6 weeks old female C57BL/6 mice (Harlan Laboratories), maintained on a folate-deficient diet were anaesthetized with isoflurane, and 50 µL of bleomycin (2 U/kg body weight) dissolved in saline was intratracheally instilled into each mouse. Healthy control mice were similarly intratracheally instilled with 50 µL saline.

Figure 4:
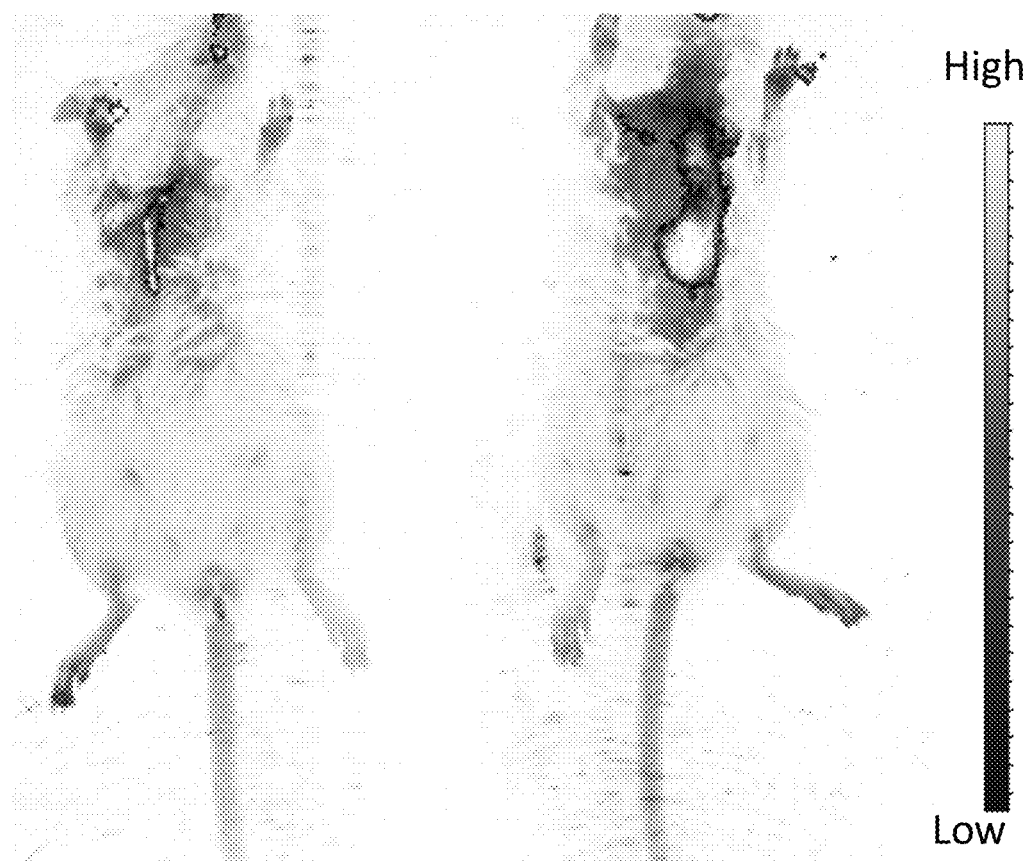
FIG. 4 illustrates a comparison of disease accumulation and disease specificity after injection of 10 nmol Pte-Tyr-S0456 (OTL-0038) in healthy mouse (left) and mouse having pulmonary fibrosis (right).

On Day 15, mice received an i.p. injection of 10 nmol OTL38. After 4 hours, mice were euthanized and imaged on an IVIS lumina II (as shown in FIG. 4).

It will be apparent to those skilled in the art that various changes may be made in the disclosure without departing from the spirit and scope thereof, and therefore, the disclosure encompasses embodiments in addition to those specifically disclosed in the specification, but only as indicated in the appended claims.

The invention claimed is:

1. A method of imaging an inflammatory disease comprising the steps of:
   a. administering to a patient in need of an effective amount of a compound capable of binding to an inflammatory cell having the formula:

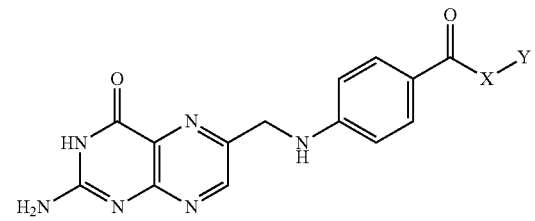

or a pharmaceutically acceptable salt or isotope thereof, wherein:
   X is an single amino acid or a single amino acid derivative thereof, wherein the single amino acid or single amino acid derivative contains an —OH, —NH$_2$, or —SH functional group wherein the amino acid of the compound is selected from the group consisting of tyrosine, cysteine, serine, lysine, a derivative of tyrosine, a derivative of cysteine, a derivative of serine and a derivative of lysine, and
   Y is a dye that has a fluorescence excitation and emission spectra in the near infra red range, wherein Y is represented by the formula:

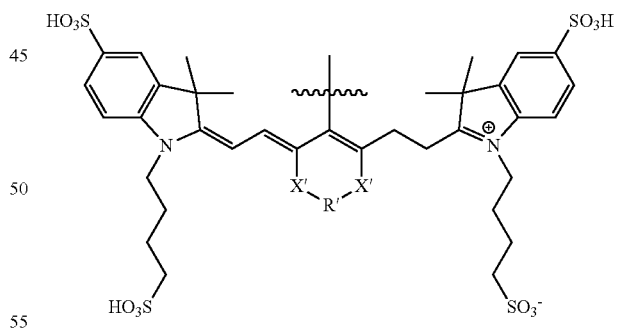

wherein, X' is independently selected from the group consisting of O, S, N and C, and
R' is independently selected from the group consisting of CH$_2$ and CH$_2$CH$_2$,
and the compound enhances the fluorescence of the dye, Y; and
   b. fluorescent imaging of an area of the inflammatory disease in the patient's body where the compound has been bound to an inflammatory cell.

2. The method of claim 1 wherein the amino acid of the compound is tyrosine.

3. The method of claim 1 wherein the amino acid derivative of the compound is a derivative of tyrosine selected from the group consisting of:

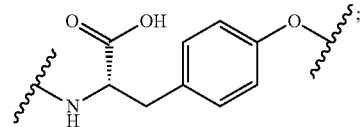

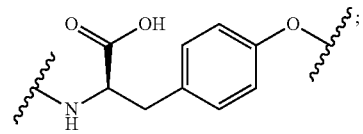

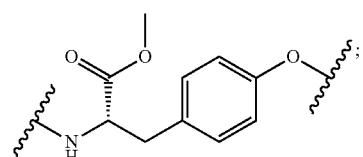

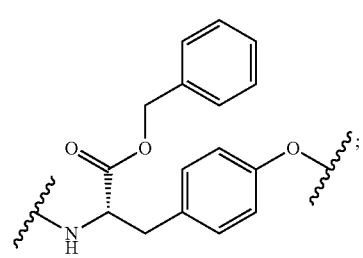

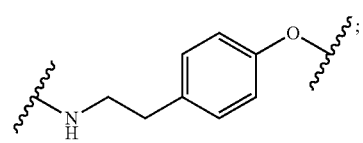

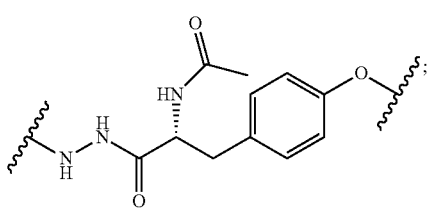

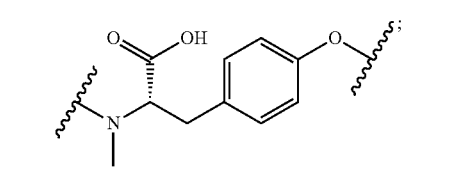

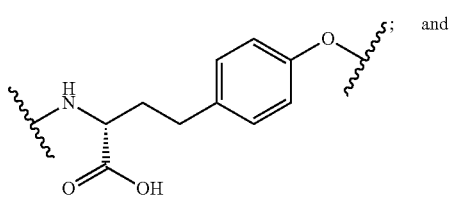

-continued

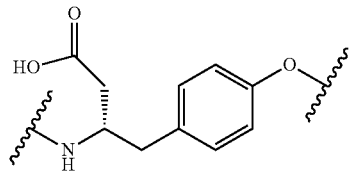

and racemic mixtures thereof.

4. The method of claim 1 wherein Y is selected from the group consisting of LS288, IR800, SP054, S0121, KODAK, IRD28, S2076, S0456 and derivatives thereof.

5. The method of claim 4 wherein the Y is S0456.

6. The method of claim 1 wherein the inflammatory cell is selected from the group consisting of activated macrophages, monocytes, and progenitor cells.

7. The method of claim 6 wherein the inflammatory cell is an activated macrophage.

8. The method of claim 7 wherein the activated macrophage is located in the patient's joints, arteries, lungs or gastrointestinal tract.

9. The method of claim 1 wherein the inflammatory disease is selected from the group consisting of: ulcerative colitis, rheumatoid arthritis, pulmonary fibrosis, atherosclerosis, multiple sclerosis, lupus erythematosus, psoriasis, osteomyelitis, Crohn's disease, graft versus host disease (GVHD), fibromyalgia, osteoarthritis, sarcoidosis, systemic sclerosis, Sjogren's syndrome, inflammations of the skin (e.g., psoriasis), glomerulonephritis, proliferative retinopathy, restenosis, and chronic inflammations.

10. The method of claim 9 wherein the inflammatory disease is ulcerative colitis.

11. The method of claim 9 wherein the inflammatory disease is rheumatoid arthritis.

12. The method of claim 9 wherein the inflammatory disease is atherosclerosis.

13. The method of claim 9 wherein the inflammatory disease is pulmonary fibrosis.

14. The method of claim 1 wherein the administration of the compound is by intravenous (I.V.) injection, intraperitoneal (I.P.) injection, or oral administration into a body part affected by an inflammatory disease.

15. The method of claim 1 further comprising delaying the imaging step for a period of time for the effective amount of the compound to target the inflammatory disease, wherein the period of time is at least about 20 minutes.

16. The method of claim 15 wherein the period of time necessary for the effective amount of the compound to target the inflammatory disease is within the range of about 20 minutes to about 2 hours.

17. A method of imaging an inflammatory disease comprising the step of:
    administering to a patient in need of an effective amount of a compound capable of binding to an inflammatory cell having the formula

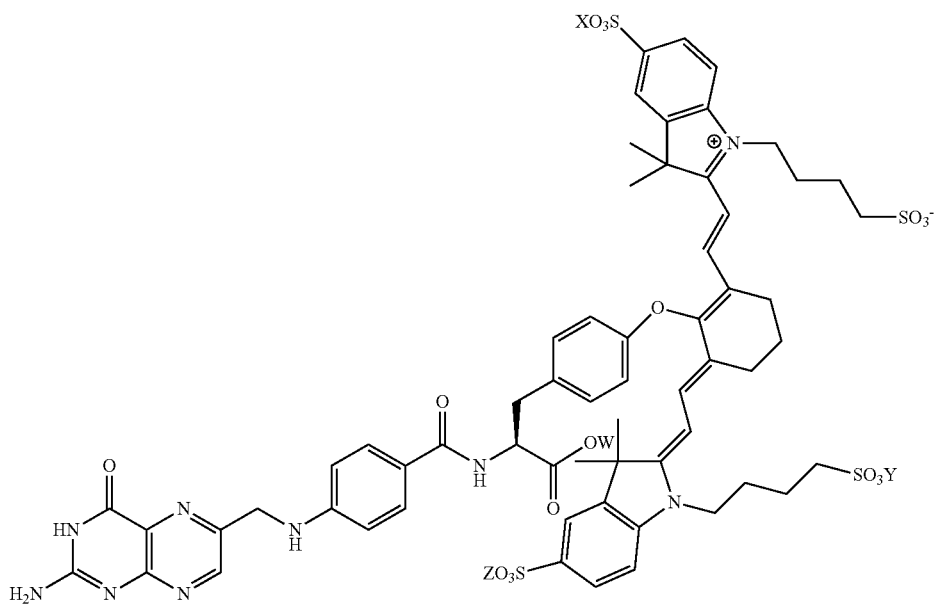

wherein W, X, Y, Z each are H, Na, K⁺ or $NH_4^+$; and b. fluorescent imaging of an area of the inflammatory disease in the patient's body where the compound has been bound to an inflammatory cell.

18. The method of claim 17 wherein the inflammatory cell is selected from the group consisting of activated macrophages, monocytes, and progenitor cells.

19. The method of claim 18 wherein the inflammatory cell is an activated macrophage.

20. The method of claim 19 wherein the activated macrophage is located in the patient's joints, arteries, lungs or gastrointestinal tract.

21. The method of claim 20 wherein the activated macrophage is located in an interphalangeal joint, metatarsophalangeal joint, wrist, elbow, shoulder, knee, ankle or fingers, thump.

22. The method of claim 17 wherein the inflammatory disease is rhiz-arthrosis, osteoarthritis, gout, or lupus.

23. The method of claim 17 wherein the inflammatory disease is selected from the group comprising ulcerative colitis, rheumatoid arthritis, pulmonary fibrosis, atherosclerosis, multiple sclerosis, lupus erythematosus, psoriasis, osteomyelitis, Crohn's disease, graft versus host disease (GVHD), fibromyalgia, osteoarthritis, sarcoidosis, systemic sclerosis, Sjogren's syndrome, inflammations of the skin (e.g., psoriasis), glomerulonephritis, proliferative retinopathy, restenosis, and chronic inflammations.

24. The method of claim 23 wherein the inflammatory disease is ulcerative colitis.

25. The method of claim 23 wherein the inflammatory disease is rheumatoid arthritis.

26. The method of claim 23 wherein the inflammatory disease is atherosclerosis.

27. The method of claim 23 wherein the inflammatory disease is pulmonary fibrosis.

* * * * *